(12) United States Patent
Wingard et al.

(10) Patent No.: US 11,635,635 B2
(45) Date of Patent: Apr. 25, 2023

(54) FOG SHIELD FOR A DIAGNOSTIC OPHTHALMIC LENS AND METHOD

(71) Applicant: SacWing Technologies, LLC, Naperville, IL (US)

(72) Inventors: Jeremy Wingard, Wayne, IL (US); Bradley Sacher, Naperville, IL (US)

(73) Assignee: SacWing Technologies LLC, Naperville, IL (US)

( * ) Notice: Subject to any disclaimer, the term of this patent is extended or adjusted under 35 U.S.C. 154(b) by 373 days.

(21) Appl. No.: 16/915,685

(22) Filed: Jun. 29, 2020

(65) Prior Publication Data
US 2021/0405391 A1  Dec. 30, 2021

(51) Int. Cl.
*G02B 1/10* (2015.01)
*G02C 7/02* (2006.01)
*G02C 7/08* (2006.01)

(52) U.S. Cl.
CPC .............. *G02C 7/024* (2013.01); *G02B 1/10* (2013.01); *G02C 7/088* (2013.01)

(58) Field of Classification Search
CPC ........ G02C 7/024; G02C 7/088; G02C 11/08; G02B 1/10; G02B 27/0006; G03B 11/045; A61B 3/028; A61B 3/04; C09D 163/00; C09D 5/006; C09D 7/62; C09D 183/06; C09D 183/08; C09D 4/00; C09D 5/008; C09D 7/67; C09D 201/00; C09D 7/40; C09D 7/63
See application file for complete search history.

(56) References Cited

U.S. PATENT DOCUMENTS

| 1,848,879 A * | 3/1932 | Halbasch ............. G03B 11/045 359/612 |
| 5,294,954 A * | 3/1994 | Nomura .................. G02B 7/04 359/612 |
| 2017/0339351 A1* | 11/2017 | Jung ........................ H04N 5/33 |

* cited by examiner

*Primary Examiner* — Mustak Choudhury
(74) *Attorney, Agent, or Firm* — Erickson Law Group, PC

(57) ABSTRACT

A fog shield for a diagnostic ophthalmic lens is disclosed. The shield has a lens mount and an air barrier. The lens mount is configured to connect to a diagnostic ophthalmic lens. The air barrier is connected to the lens mount and extends in front of the lens mount. The air barrier is located below and in front of the diagnostic ophthalmic lens when the lens mount is connected to the diagnostic ophthalmic lens.

20 Claims, 21 Drawing Sheets

FOG SHIELD FOR A DIAGNOSTIC OPHTHALMIC LENS AND METHOD

FIELD OF THE INVENTION

This invention relates in general to a fog shield for a diagnostic ophthalmic lens.

BACKGROUND OF THE INVENTION

Diagnostic ophthalmic lenses are used by eyecare personnel, such as ophthalmologists and optometrists, to examine a patient's eye and to diagnose diseases and ailments of the eye. Such lenses can be moved close to a patient's eye to be examined in order for the eyecare professional to obtain his or her desired view of the patient's eye or a portion(s) thereof.

The present inventors recognized that a patient's respiration can cause a diagnostic ophthalmic lens to fog during an eye examination, thus obscuring the desired and clear view of the patient's eye. The present inventors recognized that when a patient wears a mask that covers the patient's mouth and/or nose during examination, the exhaled breath escaping from the mask of the patient can fog, i.e. cause condensation on, the diagnostic ophthalmic lens. The present inventors recognized that fogging of the lens impedes and slows examination due to the need to clean the lens and remove the condensation from the lens. This fog cleaning may be required multiple times during an examination. The present inventors recognized the need for a device and method that prevents fogging of diagnostic ophthalmic lens during an examination of a patient's eye while allowing the patient to continue to wear a mask.

SUMMARY OF THE INVENTION

A fog shield for a diagnostic ophthalmic lens is disclosed. The shield has a lens mount and an air barrier. The lens mount is configured to connect to a diagnostic ophthalmic lens. The air barrier is connected to the lens mount and extends in front of the lens mount. The air barrier is located below and in front of the diagnostic ophthalmic lens when the lens mount is attached to the diagnostic ophthalmic lens.

A method of preventing fogging of a diagnostic ophthalmic lens is disclosed.

An air barrier is mounted to a diagnostic ophthalmic lens so that the air barrier is located below the lens and extends forward from a front of the lens creating a blocked zone above the barrier and in front of the lens. The lens with the barrier is moved toward a patient's eye wherein the barrier blocks the patient's exhaled breath from the blocked zone in front of the lens.

Numerous other advantages and features of the present invention will become readily apparent from the following detailed description of the invention and the embodiments thereof, from the claims, and from the accompanying drawings.

DETAILED DESCRIPTION

Figure 1:
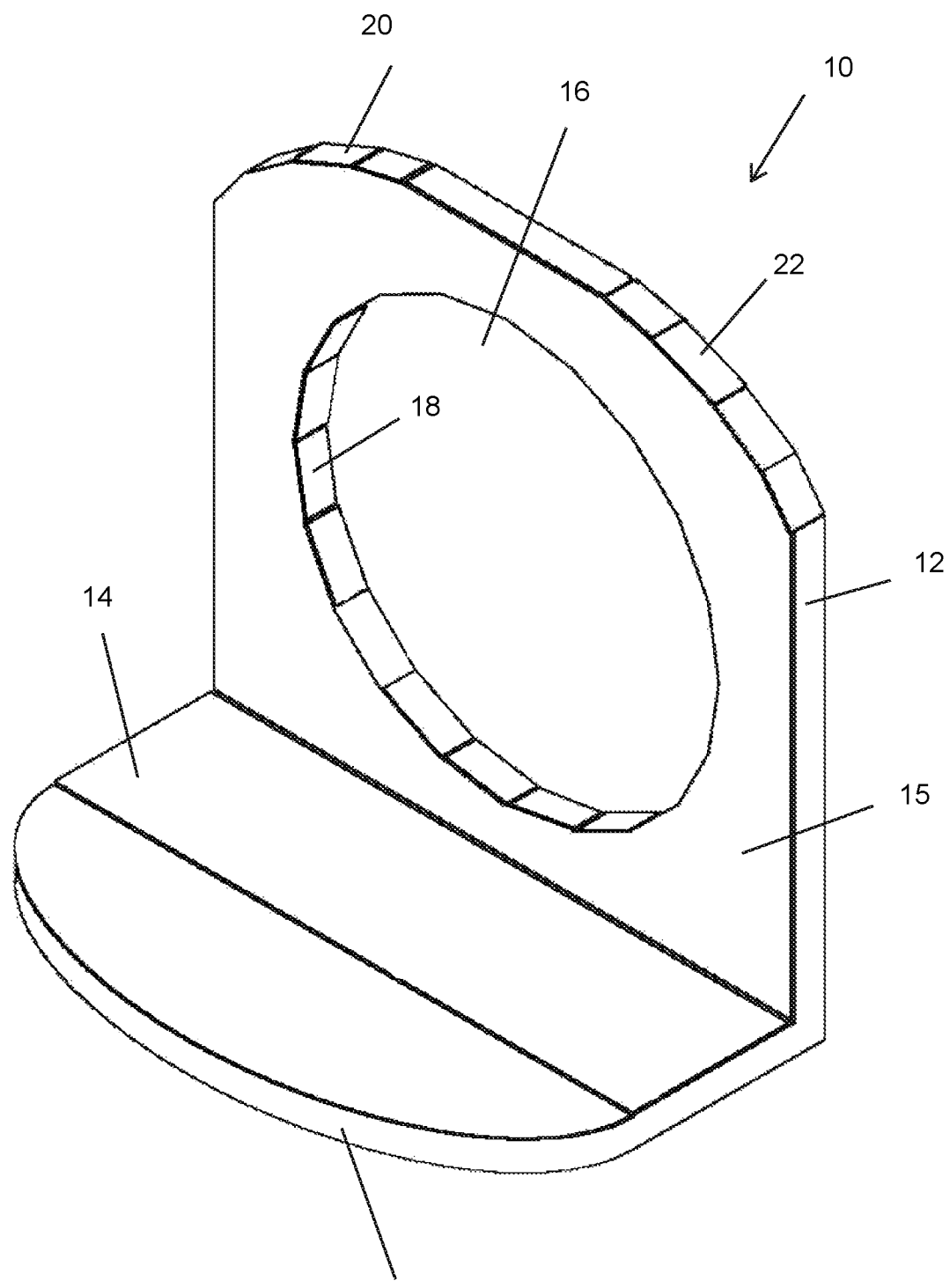
FIG. 1 is a front perspective view of a first embodiment fog shield for a diagnostic ophthalmic lens of the invention.

The following description is presented to enable any person skilled in the art to make and use the invention. For the purposes of explanation, specific nomenclature is set forth to provide a plural understanding of the present invention. While this invention is susceptible of embodiment in many different forms, this description describes and the drawings show specific embodiments of the invention with the understanding that the present disclosure is to be considered as an exemplification of the principles of the invention and is not intended to limit the invention to the specific embodiments illustrated.

FIGS. 1 to 4 show a first embodiment fog shield 10 for a lens. The fog shield 10 comprises a lens mount 12 and an air barrier 14.

The lens mount 12 comprises a wall 15 with a lens aperture 16. An aperture perimeter wall 18 provides a boundary between the wall 15 and the aperture 16. In some embodiments, the wall 15 comprises a curved top 20, 22. In some embodiments, the aperture is circular.

The air barrier 14 extends transverse from the wall 15. The air barrier extends forward from the wall 15. In some embodiments, the air barrier 14 is perpendicular to the wall 15. In some embodiments, the barrier 14 is joined or integrally formed with the wall 15. In some embodiments, a front 24 of the barrier 14 is curved.

Figure 2:
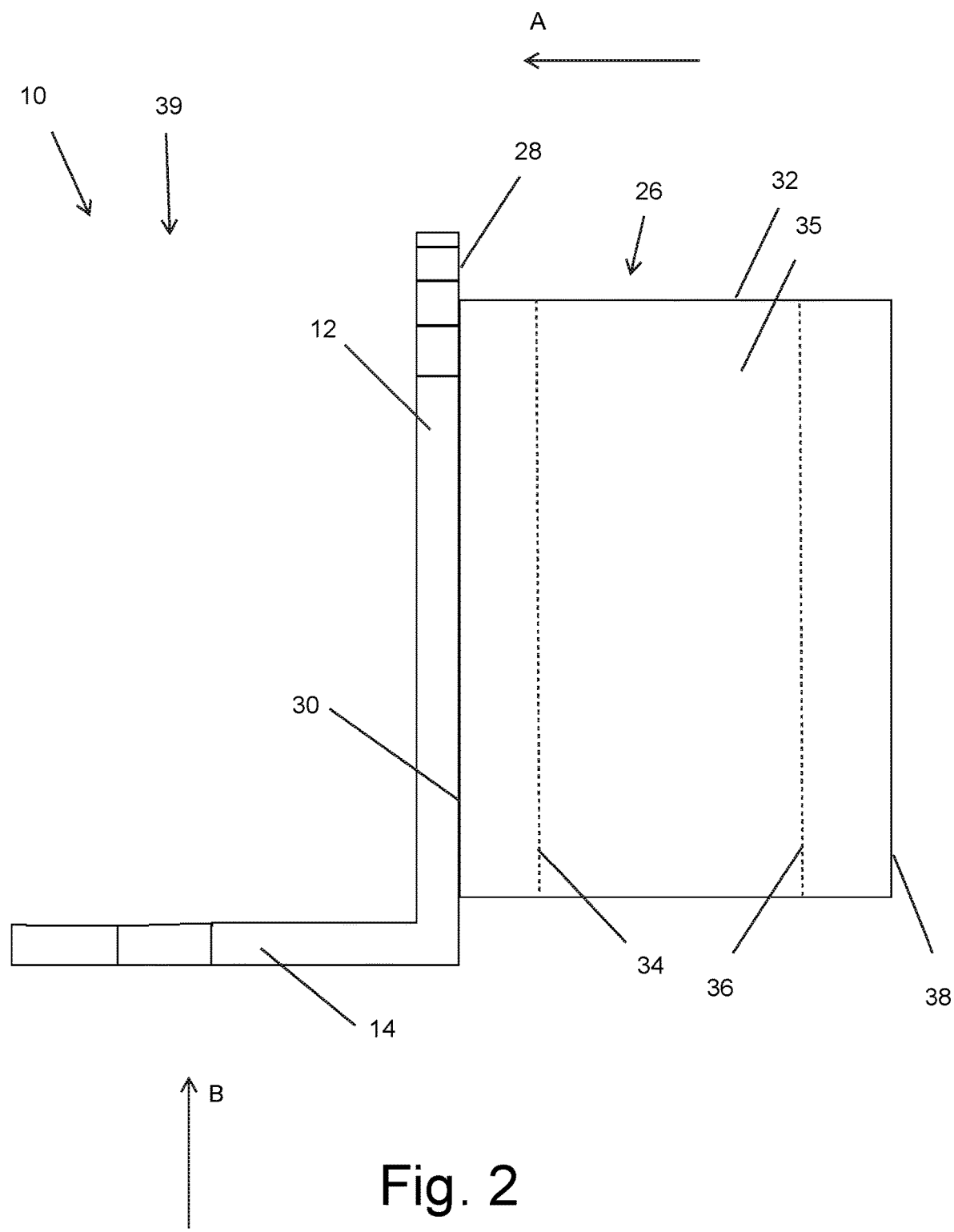
FIG. 2 is a side view of the shield of FIG. 1 joined to a diagnostic ophthalmic lens.

The fog shield 10 is mountable to a lens, such as lens unit 26, shown in FIG. 2, and more particularly, a diagnostic ophthalmic lens. In some embodiments and applications, the lens unit 26 comprises a housing 32 containing a diagnostic ophthalmic lens 35. The back wall 28 of the wall 15 is mounted to the front lip or face 30 of the lens housing 32 of the lens unit 26. In some embodiments, the front surface 34 of the lens 35 of the lens unit 26 is set back from the front facing lip or face 30 of the lens housing 32 of the lens unit 26. In some embodiments, the lens housing 32 surrounding and holding the optical lens is cylindrical with open ends, but other shapes are possible.

Figure 3:
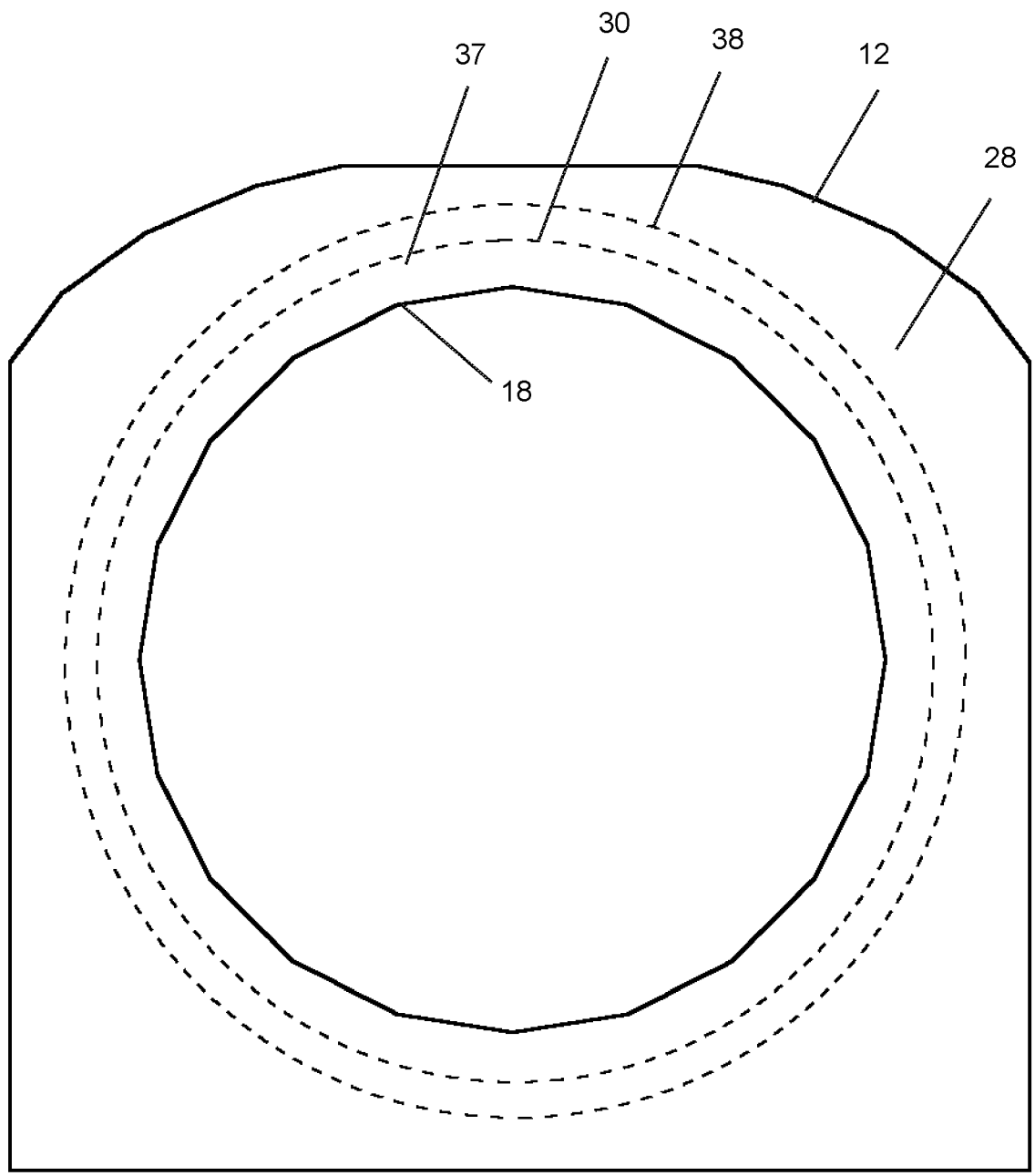
FIG. 3 is a rear view of the shield of FIG. 1.
Figure 4:
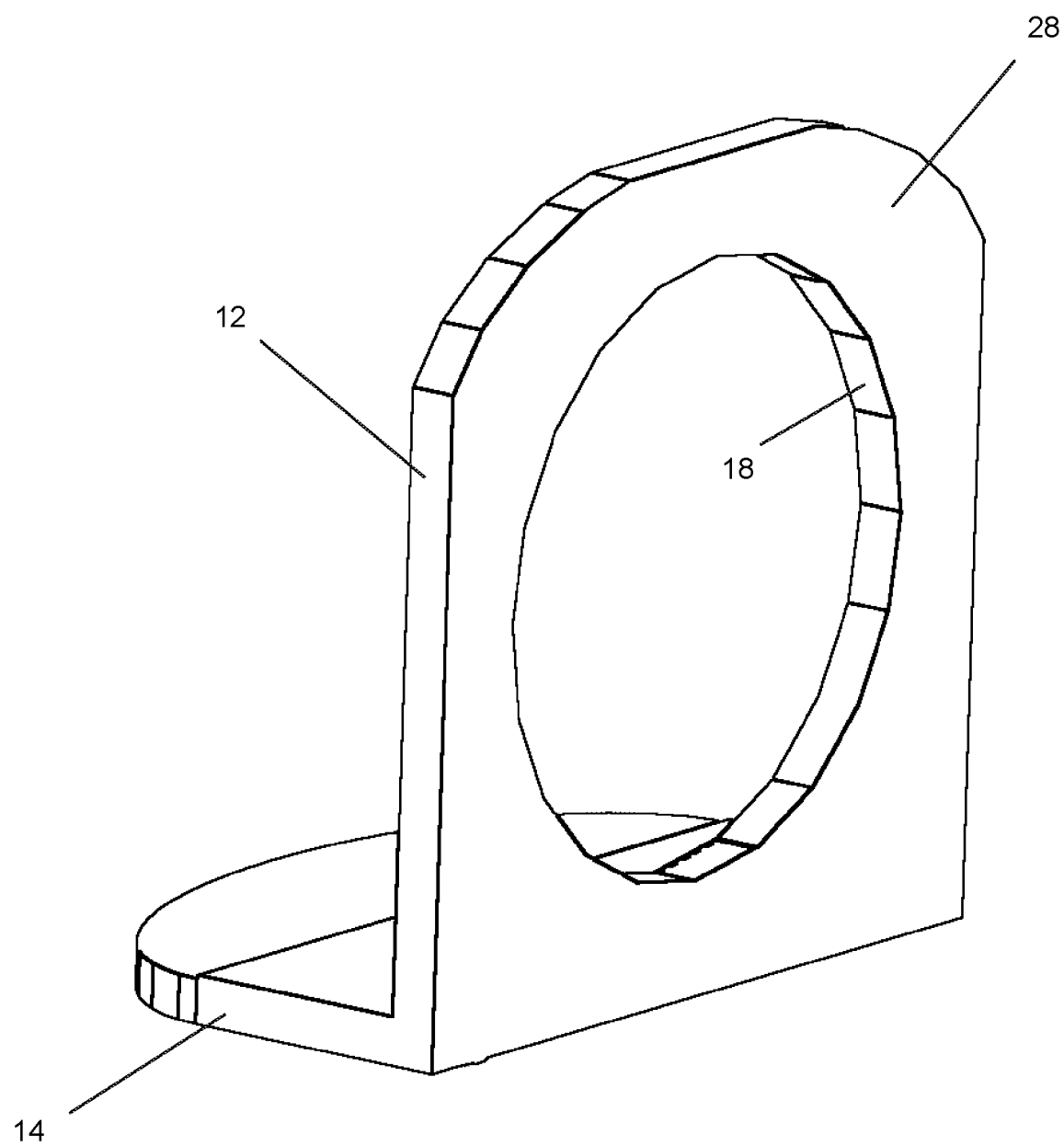
FIG. 4 is a rear perspective view of the shield of FIG. 1.

The back side 28 of the wall 15 comprises an adhesive at and/or adjacent the perimeter wall 18. In some embodiments, the back wall 28 comprises an adhesive zone 37. The adhesive zone extends between the perimeter wall 18 and an outer edge of the adhesive zone 37. As shown in FIG. 3, the front facing lip or face 30 of the lens unit 26 is within the adhesive zone 37. Therefore, the adhesive at the location(s) of contact between the back wall 28 and the front-facing lip or face 30 of the lens unit 26 joins the fog shield 10 to the lens unit 26. In some embodiments, the adhesive is located in the entire adhesive zone. In some embodiments, the adhesive is located intermittently or at one location within the adhesive zone.

In some embodiments, the adhesive releasably attaches the lens to the wall 15. Therefore, the connecting force of the adhesive can be overcome by a sufficient disconnecting force applied by the user's hand(s). In some cases, the adhesive is reusable so that the lens may be disconnected and reconnected to the wall numerous times. In embodiments, the adhesive comprises sticky tack, glue, adhesive resin, tape, or other known attachment vehicles.

Figure 22:
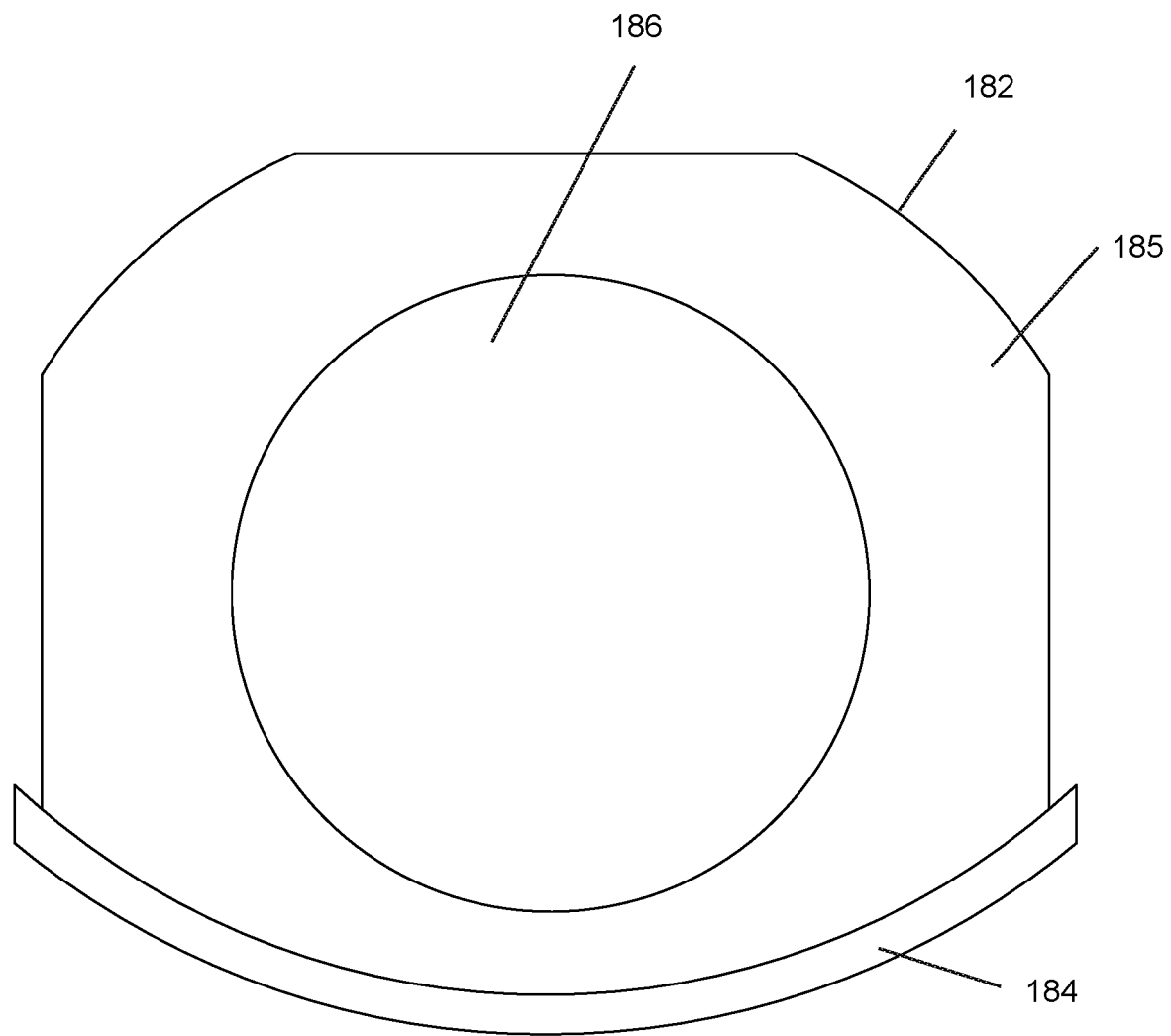
FIG. 22 is a front view of the fog shield of FIG. 19.

The lens unit 26 may comprise any desired lens, including any diagnostic ophthalmic lens. The back 36 of the optical lens is set forward from the back-facing lip or face 38. Therefore, the lens can extend between the front 34 and the back 36. While the front 34 and back 36 of the lens are shown flat in FIG. 22, in some applications the front and/or back comprise a simple curve, such as a profile of a portion of a sphere or cylinder, or complex surface profile, such as an aspheric profile.

The housing 32 can comprise more than one lens, in which case the front 34 may be the front of a front optical lens, and the back 36 may be the back of a back optical lens.

In use, the fog shield is fixed to extend in front of the lens housing. The user, such as an ophthalmologist or optometrist, holds the housing of the lens. The user moves the housing with the fog shield toward an eye of a patient or person to be examined. The lens is aligned with the patient's eye. The lens is moved close enough to the patient's eye for the user to obtain the view of the patient's eye that is desired. The front 24 of the barrier 14 may be in close proximity to or in contact with the patient's face below the patient's eye to be examined through the lens. The user will have a line of sight (in the direction A) through the lens, through the aperture 16 of the wall 15 to and/or into the patient's eye.

The barrier 14 will block exhaled breath of the patient from reaching the front surface 34 of the lens unit 26 and fogging, condensing, and/or depositing liquid or debris thereon. During respiration, exhaled air can be warmer and comprising more moisture or humidity than the surrounding ambient air. Warm air rises. So exhaled respiration of the patient can rise toward the patient's eyes. This occurs to a greater extent when the patient is wearing a mask that covers the patient's mouth and/or nose. If the mask does not tightly seal to the user's face along the top of the mask, exhaled air escapes between the wearer's face and the upper end of the mask. Without a shield, the exhaled air escaping the patient's mask can fog the front 34 of the lens, that is cause condensation on the front 34 of the lens, obscuring the user's view of the patient's eye. The fogging of the lens can occur because the exhaled breath is warmer than the front 34 surface of the lens and/or comprises higher humidity or water vapor. The warmer and/or higher humidity exhaled breath causes condensation to form on the lens in the form of small water drops of liquid forming a film on the lens, when the exhaled breath reaches the lens. When the water vapor in the exhaled breath contacts the lens it cools, given the lower temperature of the lens, causing a phase change of the water vapor to liquid on the lens surface. The lens, during examination, can be close to the top of the patient's mask, adjacent the patient's eyes, and therefore the source of the escaping exhaled breath.

The barrier 14 blocks the exhaled air (e.g. traveling up in the direction B) from reaching the front 34 of the lens or at least disperses the exhaled air a sufficient distance from the lens to prevent fogging of and condensation on the front 34 of the lens 35. Therefore, the barrier creates a blocked zone 39 above the barrier and in front of the lens. The exhaled air is either trapped below the barrier and/or forced to escape upwards beyond the horizontal boundary provided by the barrier and thus sufficiently distanced from the lens to prevent fogging of, condensation on, and the deposit of debris on the front 34 of the lens.

Figure 5:
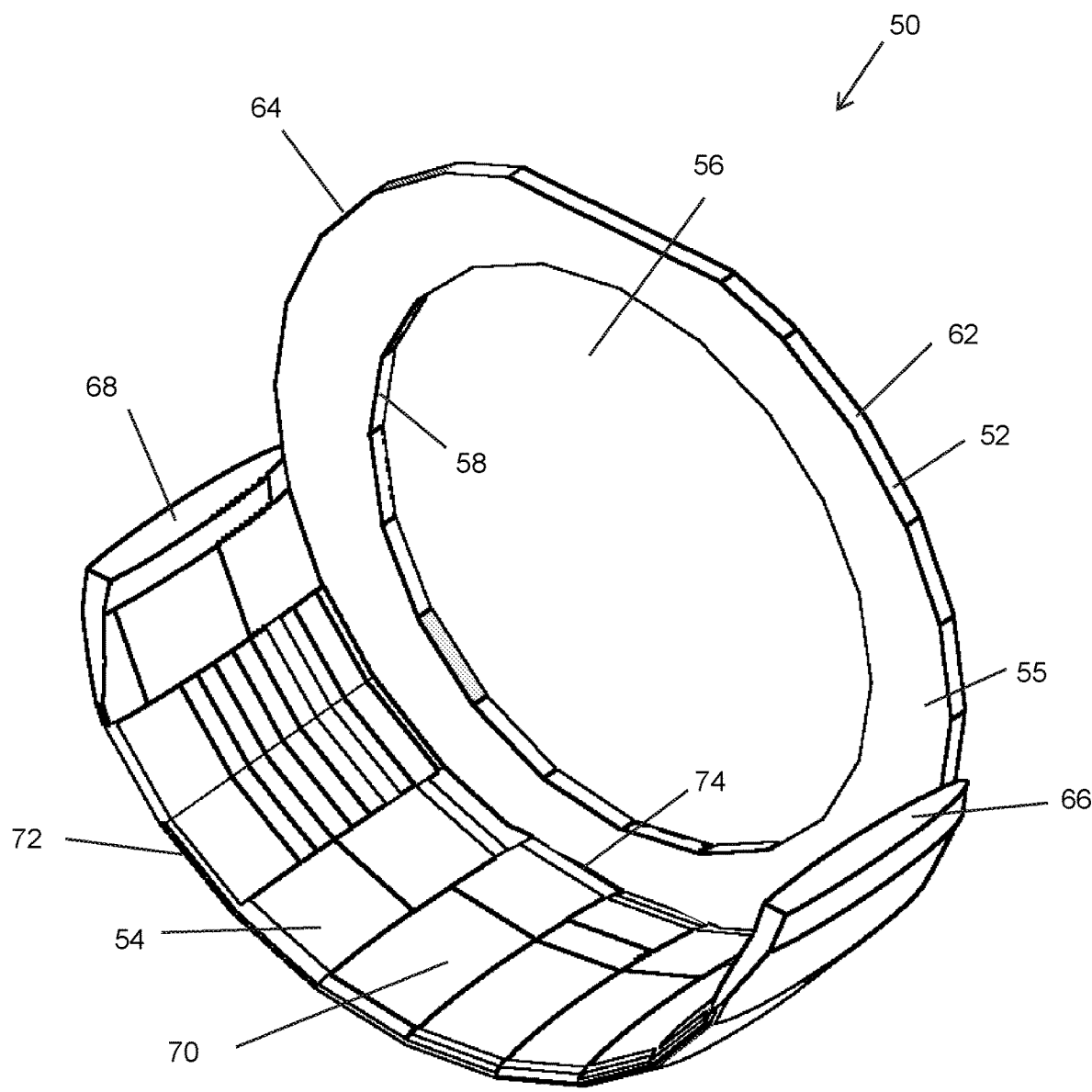
FIG. 5 is a front perspective view of a second embodiment fog shield for a diagnostic ophthalmic lens of the invention.
Figure 6:
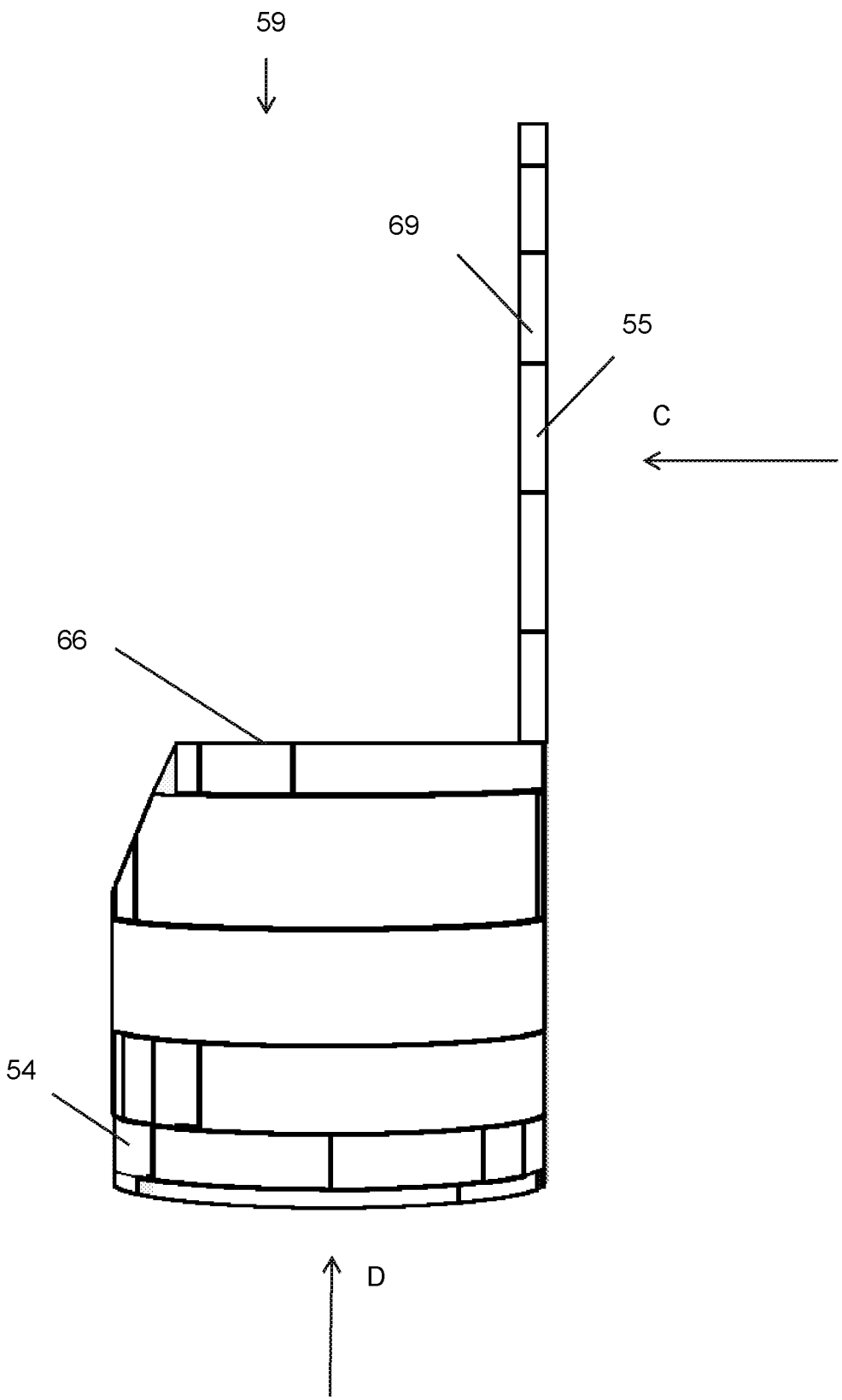
FIG. 6 is a side view of the shield of FIG. 5.

FIG. 5 shows a second embodiment fog shield 50 for a lens. The fog shield 50 comprises a lens mount 52 and an air barrier 54.

The lens mount 52 comprises a wall 55 with a lens aperture 56. An aperture perimeter wall 58 provides a boundary between the wall 55 and the aperture 56. In some embodiments, the wall 55 comprises a curved perimeter 62, 64. In some embodiments, the curved perimeter extending about the wall 55 is circular.

The barrier 54 extends transverse from the wall 55. The air barrier 54 extends forward from the wall 55. In some embodiments, the barrier 54 is perpendicular to the wall 55. In some embodiments, the barrier 54 is joined or integrally formed with the wall 55.

The barrier 54 has a curve from a first side end 66 to an opposite second side end 68. The curve follows the perimeter edge 69 of the wall 55. In some embodiments, the barrier 54 has an upper surface 70 with a convex curve from a front end 72 to a back end 74.

Figure 7:
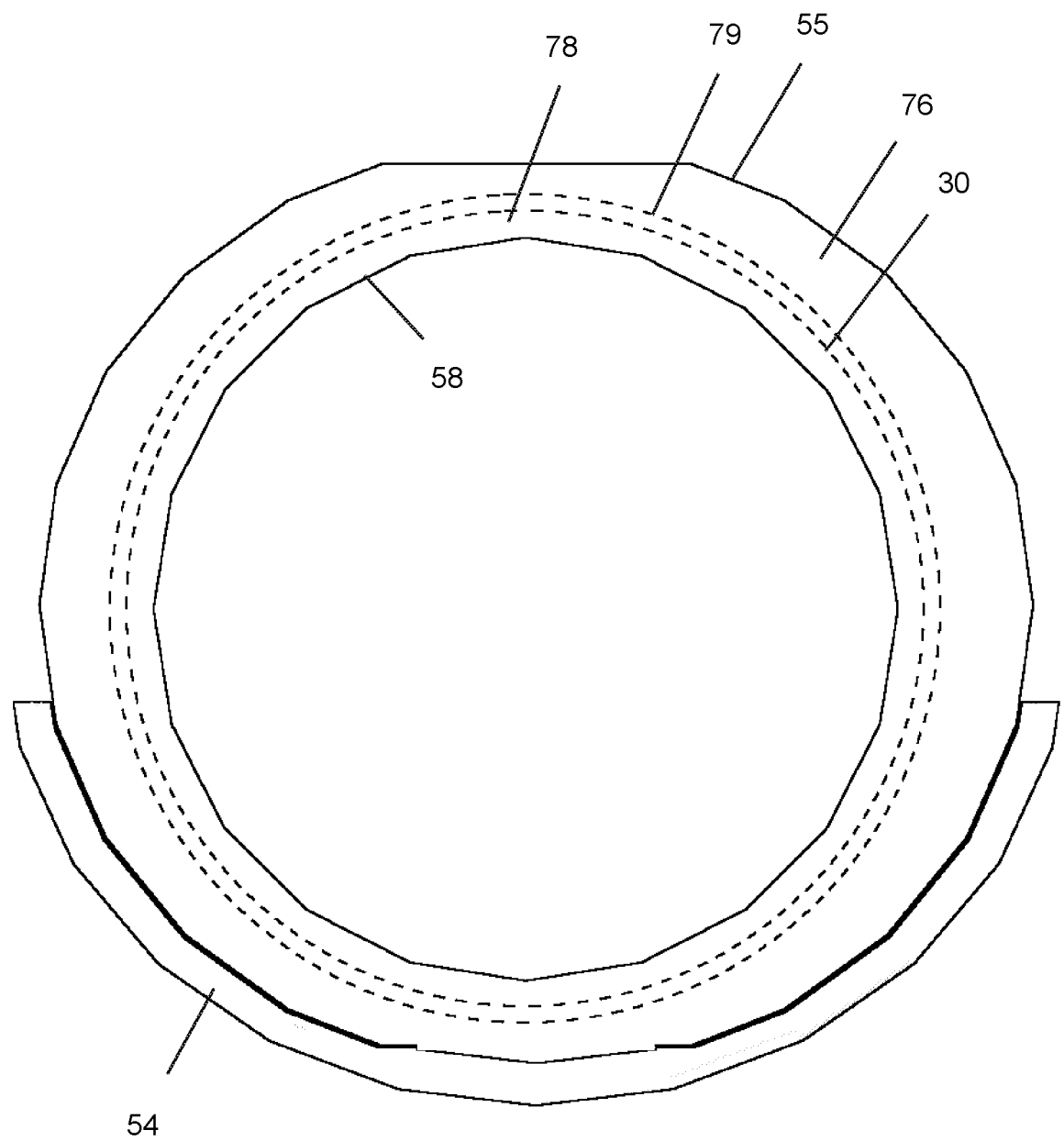
FIG. 7 is a rear view of the shield of FIG. 5.

The back side 76 of the wall 55 comprises an adhesive at and/or adjacent the perimeter wall 58. In some embodiments, the back side 76 comprises an adhesive zone 78. The adhesive zone extends between the perimeter wall 58 and an outer edge 79 of the adhesive zone 78. As shown in FIG. 7, the front facing lip or face 30 of the lens unit 26 is within the adhesive zone 78. Therefore, the adhesive at the location(s) of contact between the back wall 76 and the front-facing lip or face 30 of the housing 32 join the fog shield 50 to the lens unit 26. In some embodiments, the adhesive is located in the entire adhesive zone. In some embodiments, the adhesive is located intermittently or at one location within the adhesive zone.

Similar to fog shield 10, in use, the fog shield 50 is fixed to the front of the lens housing at the adhesive zone. The user, such as an ophthalmologist or optometrist, holds the housing of the lens. The user moves the housing with the fog shield toward an eye of a patient or person to be examined. The lens is aligned with the patient's eye. The lens is moved close enough to the patient's eye for the user to obtain the view of the patient's eye that is desired. The front end 72 of the barrier 54 may be in close proximity to or in contact with the patient's face below the patient's eye to be examined through the lens. The user will have a line of sight (in the direction C) through the lens, through the aperture 56 of the wall 55 to the patient's eye.

The barrier 54 will block exhaled breath of the patient from reaching the front surface 34 of the lens unit 26 and fogging, condensing, and/or depositing liquid or debris.

The barrier 54 blocks the exhaled air (e.g. traveling up in the direction D) from reaching the front surface 34 of the lens or at least disperses the exhaled air a sufficient distance from the lens to prevent fogging of, and condensation on, the front 34 of the lens 35. Therefore, the barrier creates a blocked zone 59 above the barrier and in front of the lens. The exhaled air is either trapped below the barrier and/or forced to escape upwards beyond the horizontal boundary provided by the barrier and thus sufficiently distanced from the lens to prevent fogging of, condensation on, and the deposit of debris on the front 34 of the lens unit 26.

Figure 8:
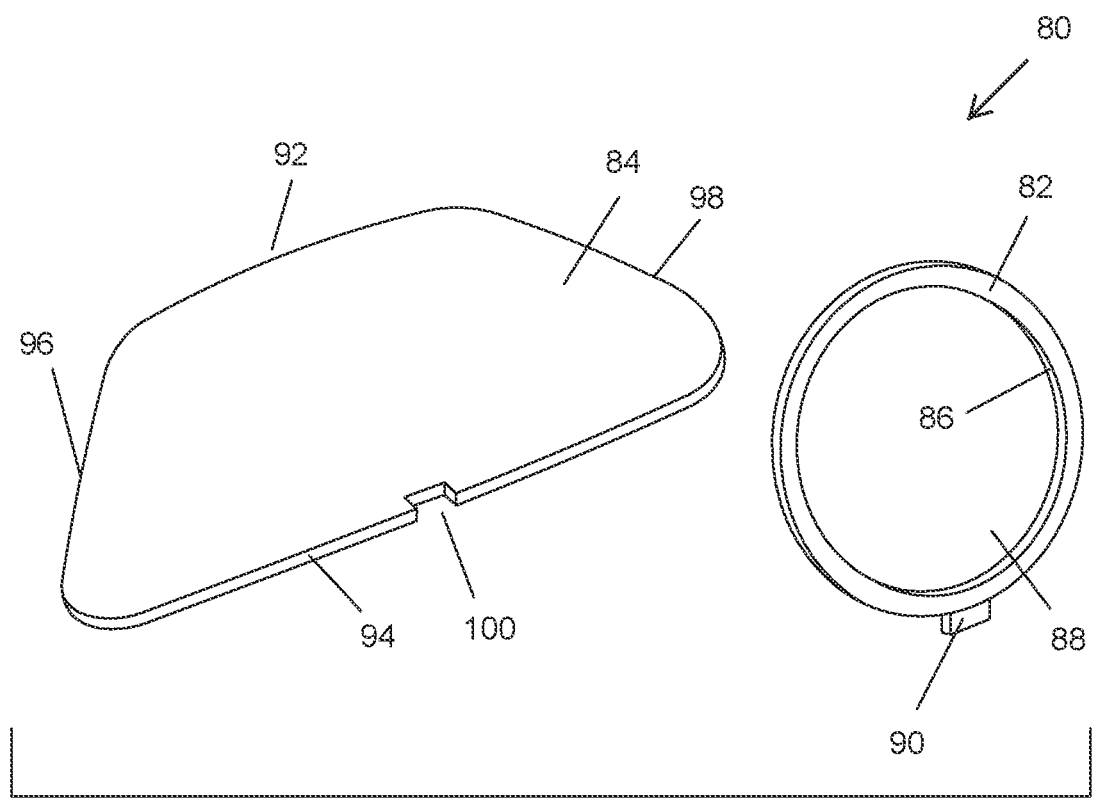
FIG. 8 is an exploded perspective view of a third embodiment fog shield for a diagnostic ophthalmic lens.

FIG. 8 shows a third embodiment fog shield 80 for a lens. The fog shield comprises a lens mount in the form of a ring 82 and an air barrier 84. The ring comprises an aperture perimeter wall 86 that forms a boundary between the ring and aperture 88 within the ring 82. The ring 82 comprises a mount protrusion 90 at the bottom of the ring as shown in FIG. 8 for engaging with the barrier 84.

FIG. 8 shows the barrier 84 comprises a trapezoid shape, and more particularly an isosceles trapezoid, with the front edge 92 shorter than the back edge 94 and the side edges 96, 98 converging from the back edge toward the front edge. But the barrier may comprise other shapes, such as quadrilateral, square, rectangle, oval, curved, irregular, or other shape.

Figure 9:
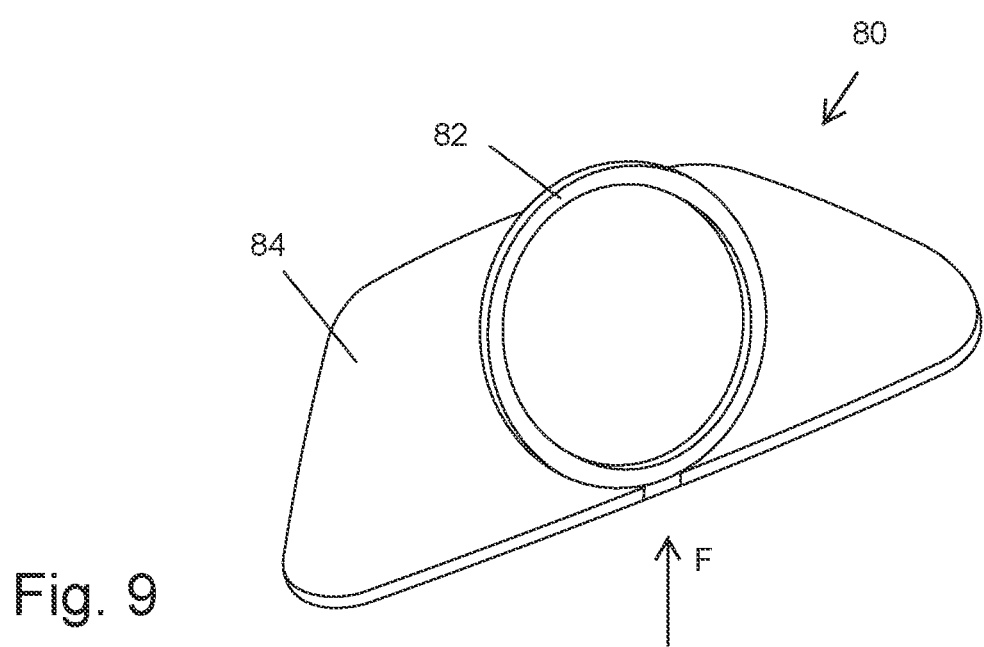
FIG. 9 is a rear perspective view of the shield of FIG. 8.

In some embodiments, the back edge 94 comprises a receiving aperture 100 for receiving the mount protrusion 90 and joining the ring 82 to the barrier. In some embodiments the ring is removably joined to the barrier 84 at the aperture 100. FIG. 9 shows the ring joined to the barrier 84.

Figure 10:
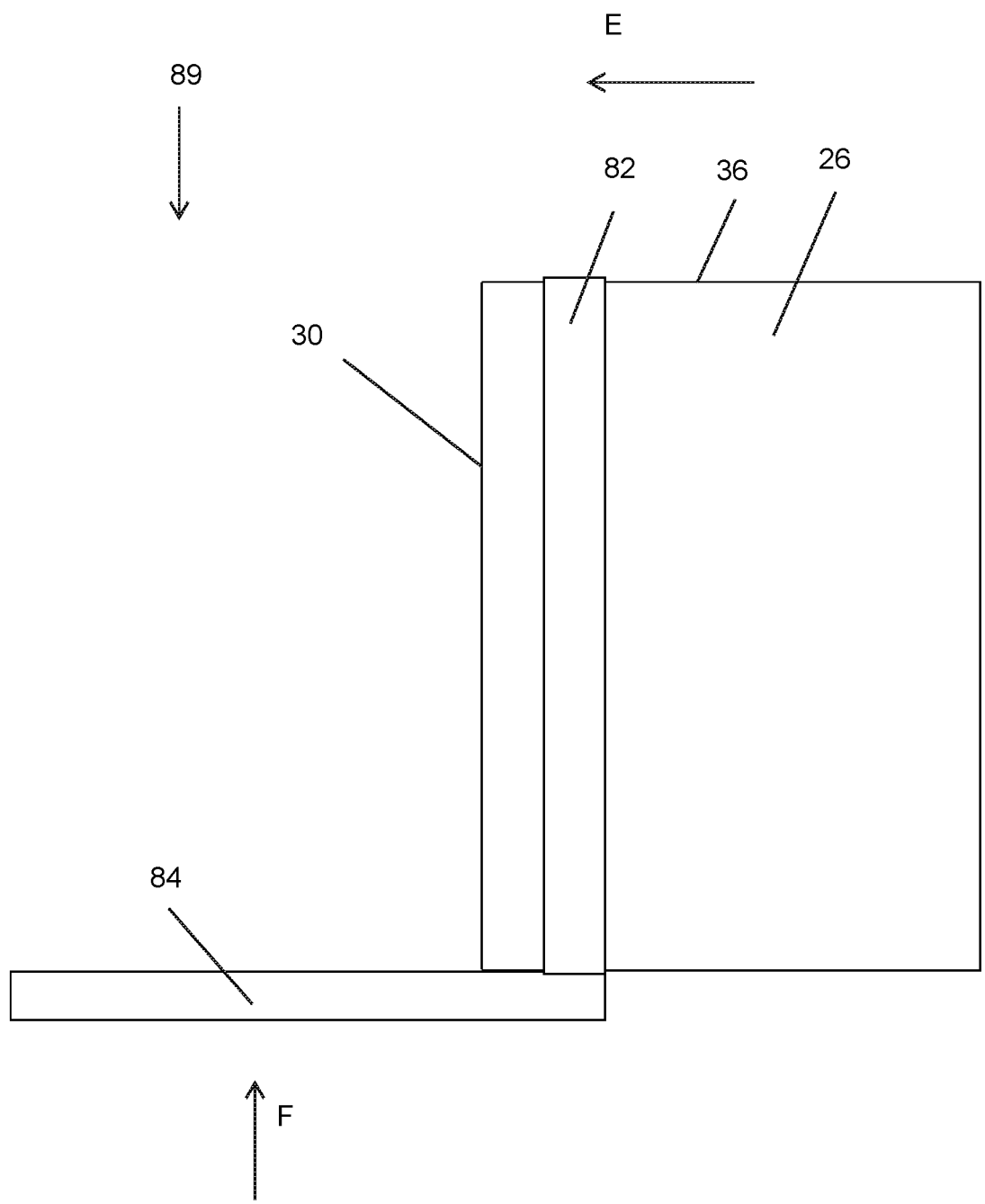
FIG. 10 is a side view of the shield of FIG. 8 mounted to a diagnostic ophthalmic lens.

FIG. 10 shows the fog shield 80 mounted to the lens unit 26. The ring extends around the exterior of the housing 36 of the lens. In some embodiments, the ring is elastic and grips the housing 36. When the ring is elastic, it can be stretched from its unstretched condition to an expanded condition where the aperture 88 is enlarged. The elastic property of the ring biases the ring to its unstretched condition. Therefore, when the size of the exterior of the housing is larger than the aperture 88 when the ring is in the unstretched condition but less than or equal to the maximum stretched condition size, then the ring can be stretched around the exterior of the housing 36 and released. There, the elastic bias of the ring will cause the ring to grip the exterior of the housing and hold the fog shield 80 to the lens unit 26. The ring and the fog shield 80 can be removed by stretching the ring and/or withdrawing the housing 36 from the aperture of the ring. While the ring 82 shown positioned back from the front face 30 of the lens, in some deployments the ring is place right at the face 30 of the housing. The ring 82 can be mounted at any location long the lens where the barrier extends beyond the face 30 of the housing to provide a blocking surface for exhaled breath of the patient.

The user of fog shield 80 will have a line of sight (in the direction E of FIG. 10) through the lens to the patient's eye, the lens occupying aperture 88 of the ring. Therefore, the ring does not obstruct the line of sight through the lens unit 26.

In the same or similar manner as described for fog shields 10, 50, when the fog shield 80 is mounted to a lens, such as lens unit 26, the barrier 84 blocks the exhaled air (e.g. traveling up in the direction F of FIG. 10) from reaching the front surface 34 of the lens or at least disperses the exhaled air a sufficient distance from the lens to prevent fogging of, and condensation on, the front 34 of the lens 35. Therefore, the barrier creates a blocked zone 89 above the barrier and in front of the lens. The exhaled air is either trapped below the barrier and/or forced to escape upwards beyond the horizontal boundary provided by the barrier and thus sufficiently distanced from the lens to prevent fogging of, condensation on, and the deposit of debris on the front 34 of the lens.

Figure 11:
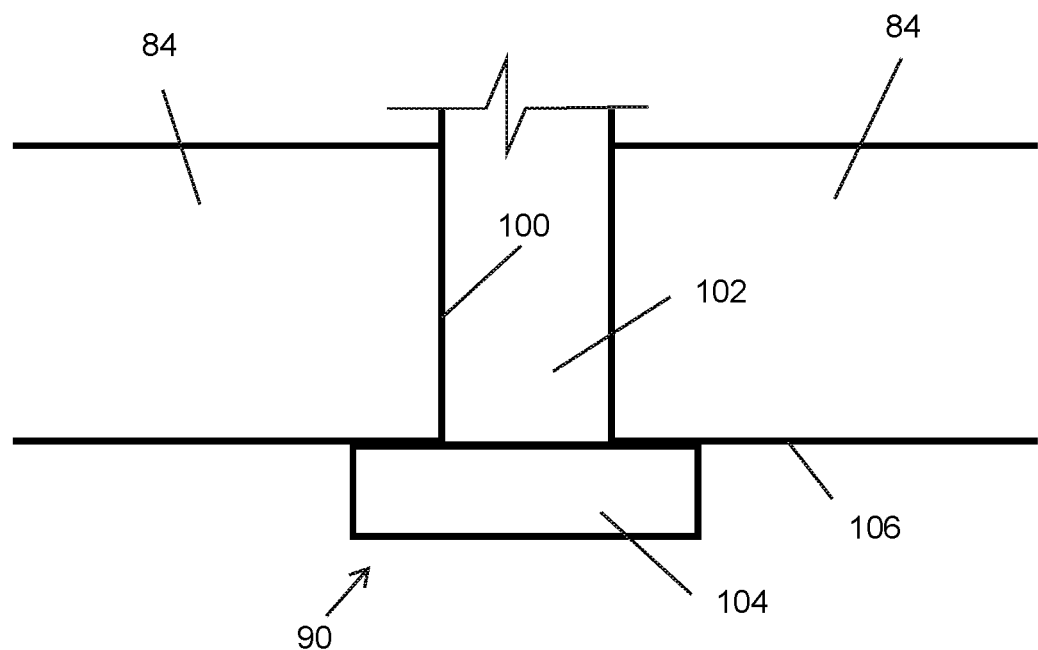
FIG. 11 is a side view of a connection between a barrier and a ring of the shield of FIG. 8.

FIG. 11 shows the protrusion 90 and the aperture 100. The aperture 100 extends through the body of the barrier 84. The protrusion 90 comprises a shaft 102 and a head 104. The head is larger than the diameter or width of the shaft and larger than the diameter or width of the aperture 100. Therefore, the head contacts the bottom wall 106 of the barrier 84 and prevents the protrusion 90 from withdrawing from the aperture 100. In some embodiments, the barrier is pivotal about the axis of the shaft for allowing positional adjustment of the barrier relative to the ring and lens about the axis of the shaft.

Figure 12:
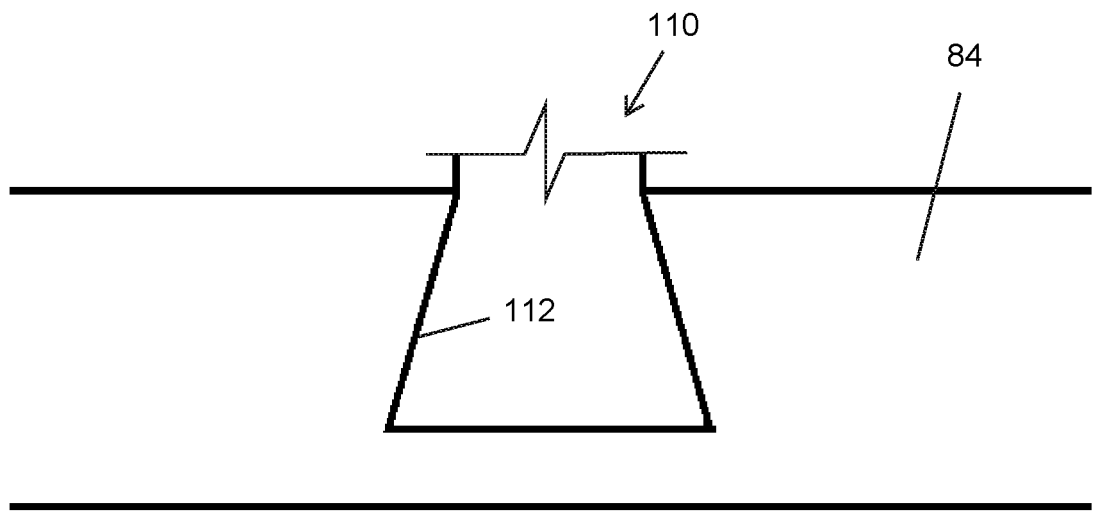
FIG. 12 is a side section view of an alternative embodiment connection between the barrier and the ring of the shield of FIG. 8.

FIG. 12 shows a second embodiment protrusion 110 usable on the ring 82 in place of protrusion 90. FIG. 12 also shows a second embodiment aperture 112 usable on barrier 84 in place of aperture 100. The protrusion 110 and aperture 112 comprise a dovetail joint. The protrusion is a flaring tenon and the aperture 112 is a mortise which receives the tenon. The narrowing sidewalls of the aperture 112 from the bottom to the top prevent the protrusion from withdrawing upward and the barrier from escaping downward. The protrusion has complementary sidewalls to the side walls of the aperture 112. The side walls of the protrusion converge from the bottom toward the top of the protrusion.

While the aperture 100 shown in FIG. 8 is in the back edge 94 of the barrier 84, in some embodiments, the back edge of the barrier is not recessed, and the aperture 100, 112 is within the body of the barrier adjacent the back edge. In this way, the side perimeter walls of the aperture 100, 112 can bound the protrusion 90, 110 on all sides, other than the top side, and in some cases, the bottom side as shown in FIG. 11. Therefore, the aperture 100, 112 can prevent or limit movement in all directions in the plane(s) of the barrier 84 relative to the protrusion. For example, when the barrier 84 is in a horizontal position, the aperture 100, 112 will prevent or limit movement in all directions in the horizontal plane(s) of the barrier 84 relative to the protrusion.

Figure 13:
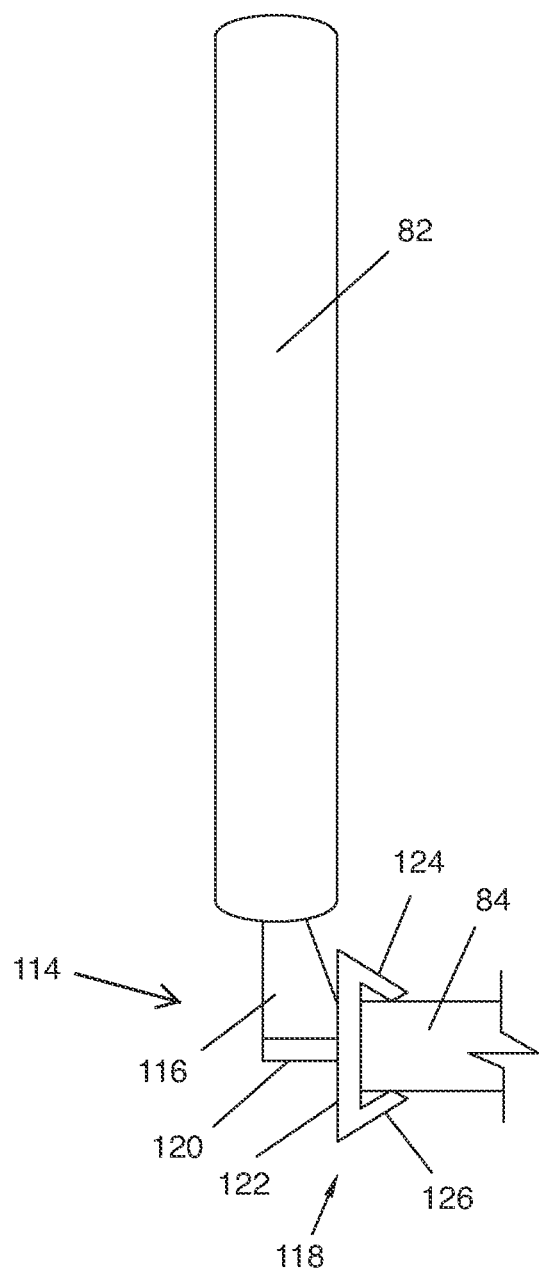
FIG. 13 is a side view of the shield of FIG. 8 with an alternative embodiment connection between the barrier and the ring of the shield of FIG. 8.

FIG. 13 shows the ring 82 with a third embodiment mounting protrusion 114. The protrusion 114 comprises a first downward portion 116 fixed to a barrier gripper 118. The gripper 118 comprises a rear projection 120 fixed to the first downward portion 116. The gripper 118 comprises a crossmember 122 joining opposite upper and lower gripper arms 124, 126. The gripper arms hold the barrier 84.

In some embodiments, the gripper arms are biased toward each other. When the thickness of the barrier 84 is greater than the distance between the gripper arms in an unflexed position, the bias of the gripper arms will compression and or friction-hold the barrier between the gripper arms. The cross member 122 provides a back stop to the barrier between the grippers.

In some embodiments, the ring 82 and the air barrier 84 are formed as one unit rather than two separate or separable parts.

Figure 14:
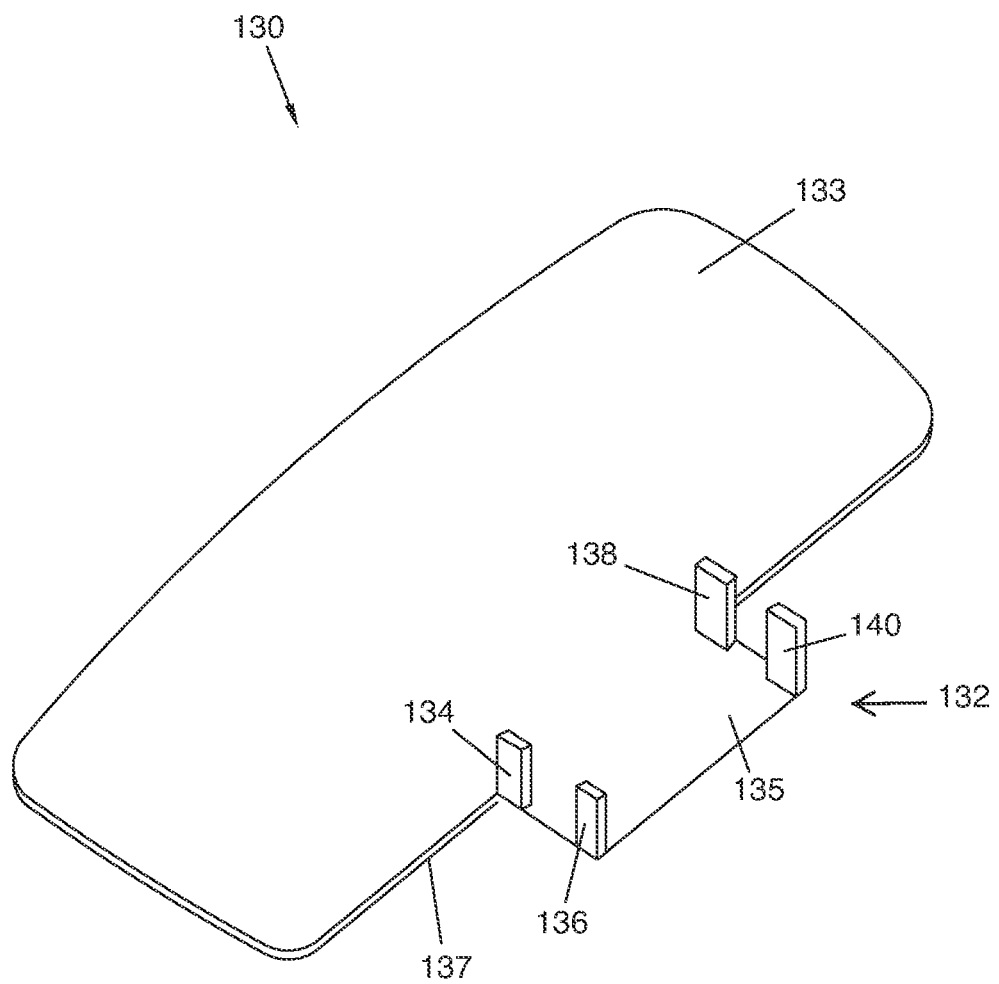
FIG. 14 is a rear perspective view of a fourth embodiment fog shield for a diagnostic ophthalmic lens of the invention.
Figure 15:
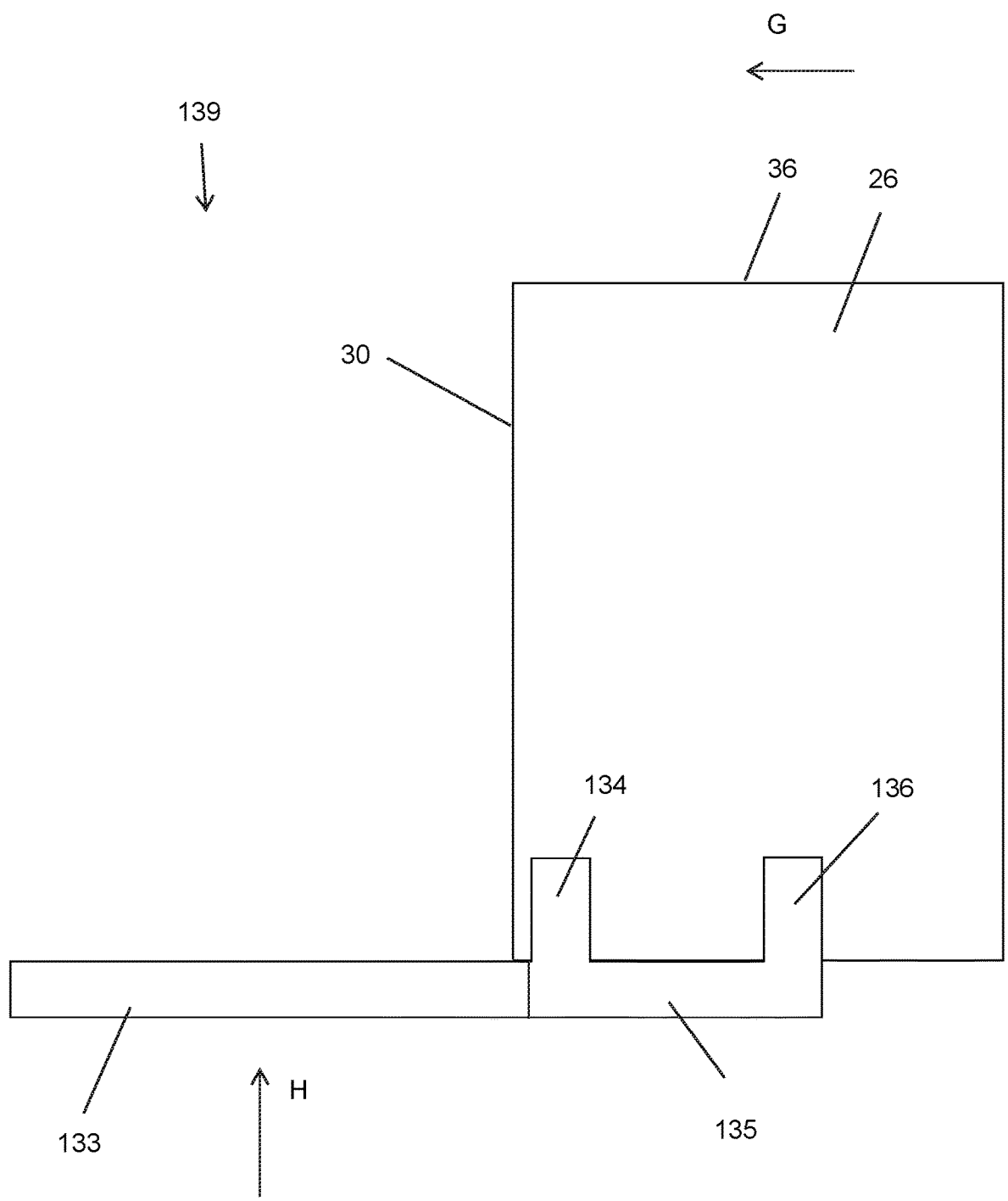
FIG. 15 is a side view of the shield of FIG. 14.

FIGS. 14 and 15 show a fourth embodiment fog shield 130. The fog shield 130 comprises a lens mount 132 and an air barrier 133. The lens mount extends from the back 137 of the barrier 133.

The lens mount 132 comprises a plurality of lens grippers 134, 136, 138, 140. In some embodiments, the grippers are located at the four corners of the base 135 of the lens mount 132.

The grippers extend upward from the base 135 to grip the housing 36 of lens unit 26. Therefore, the grippers connect the fog shield 130 to the lens unit 26.

In some embodiments, the grippers 134 and 136 are resiliently biased toward grippers 138 and 140, and the grippers 138 and 140 are resiliently biased toward grippers 134 and 136 so that lens unit 26 is gripped between the opposite grippers.

In some embodiments, the grippers comprise adhesive on the interior sides thereof which face the housing 36 of the lens. The adhesive releasably holds the grippers to the housing 36 of the lens unit 26.

The user of fog shield 130 will have a line of sight (in the direction G of FIG. 15) through the lens to the patient's eye, the barrier 133 is below the lens. Therefore, the fog shield 130 does not obstruct the line of sight through the lens.

In the same or similar manner as described for fog shields 10, 50, 80, when the fog shield 130 is mounted to a lens, such as lens unit 26, the barrier 133 blocks the exhaled air (e.g. traveling up in the direction H of FIG. 15) from reaching the front lens 34 of the lens unit 26 or at least disperses the exhaled air a sufficient distance from the lens to prevent fogging of, and condensation on, the front 34 of the lens 35. Therefore, the barrier creates a blocked zone 139 above the barrier and in front of the lens. The exhaled air is either trapped below the barrier and/or forced to escape upwards beyond the horizontal boundary provided by the barrier and thus sufficiently distanced from the lens to prevent fogging of, condensation on, and the deposit of debris on the front 34 of the lens unit 26.

Figure 16:
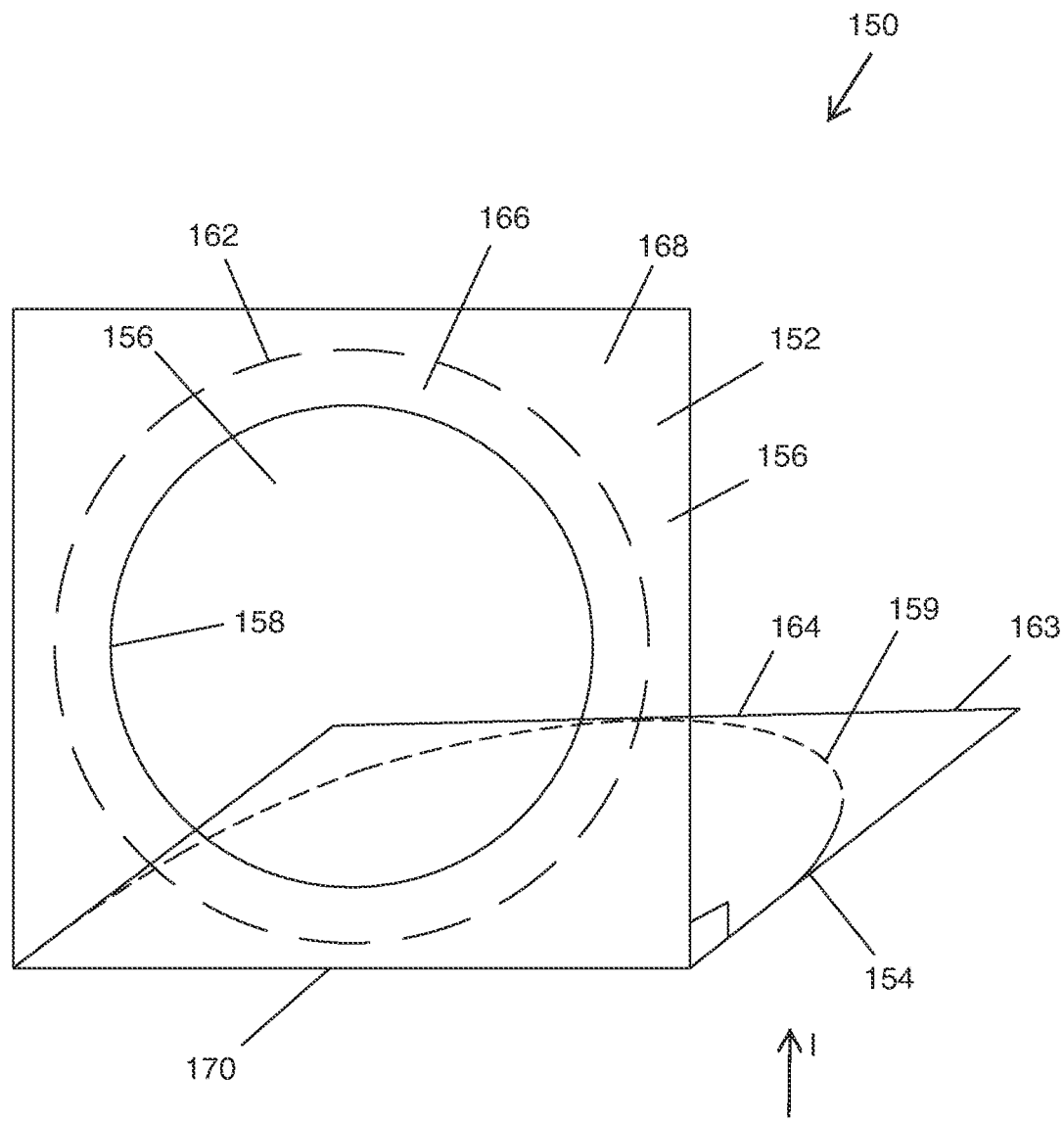
FIG. 16 is a rear perspective view of a fifth embodiment fog shield for a diagnostic ophthalmic lens of the invention.

FIG. 16 shows a fifth embodiment fog shield 150. The fog shield 150 comprises a lens mount 152 and a barrier 154.

The lens mount 152 comprises a wall 155 with a lens aperture 156. An aperture perimeter wall 158 provides a boundary between the wall 155 and the aperture 156.

The barrier 154 extends transverse from the wall 155. The barrier extends forward from the wall 155. In some embodiments, the barrier 154 is perpendicular to the wall 155. In some embodiments, the barrier 154 is joined or integrally formed with the wall 15. In some embodiments, a front 164 of the barrier 154 is curved 159. In some embodiments, the front 164 is straight 163.

The back side 168 of the wall 155 comprises an adhesive at and/or adjacent the perimeter wall 158. In some embodiments, the back side 168 comprises an adhesive zone 166. The adhesive zone extends between the perimeter wall 158 and an outer edge 162 of the adhesive zone 166. The front facing lip or face 30 of the lens unit 26 is pressed against the back side 168 within the adhesive zone 166. Therefore, the adhesive at the locations of contact between the back wall 28 and the front-facing lip or face 30 of the lens unit 26 joins the fog shield 150 to the lens unit 26. In some embodiments, the adhesive is located in the entire adhesive zone. In some embodiment, the adhesive is located intermittently or at one location within the adhesive zone.

Figures 17, 18:
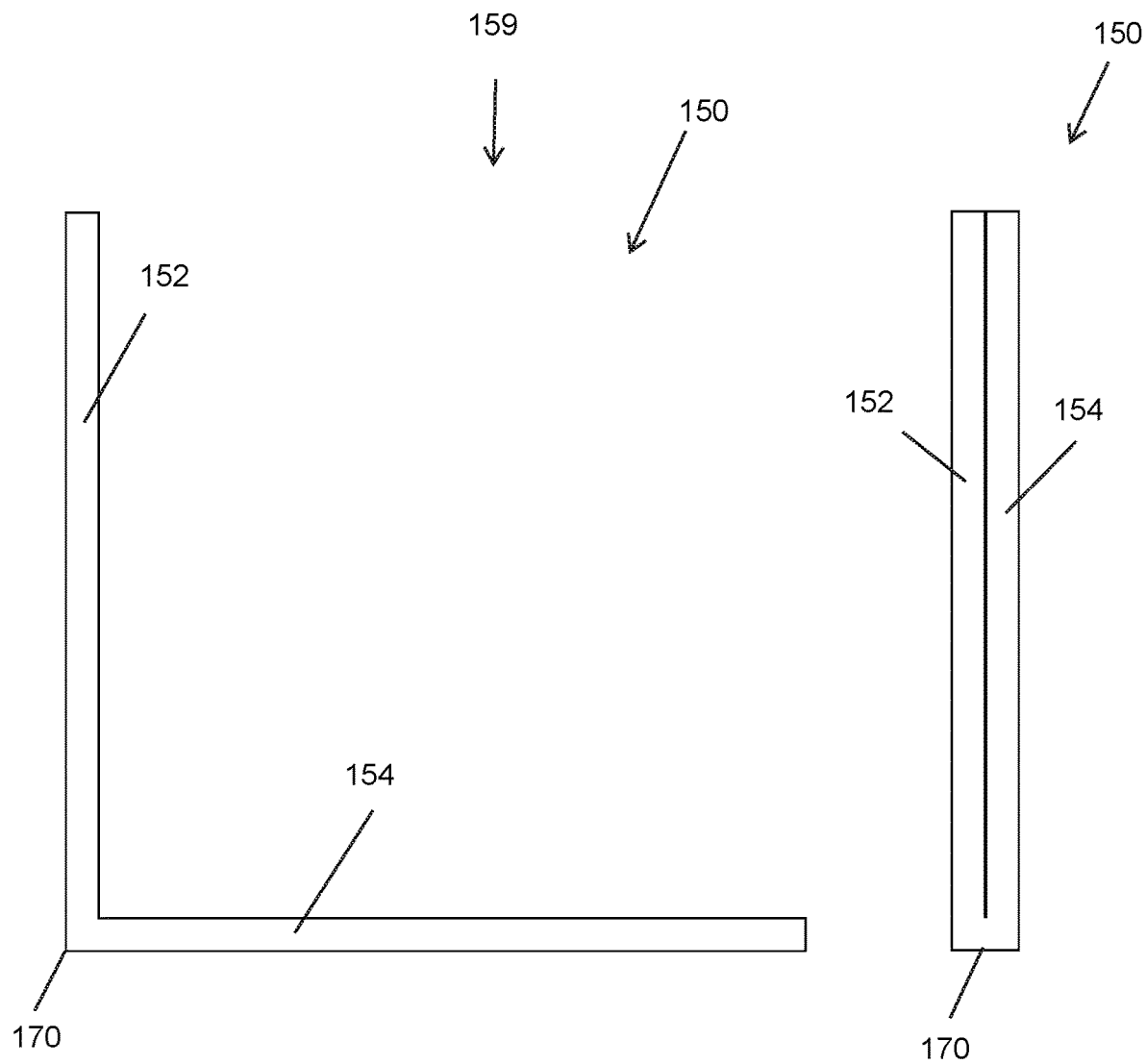
FIG. 17 is a side view of the shield of FIG. 16 in a deployed position.
FIG. 18 is a side view of the shield of FIG. 16 in a closed position.

In some embodiments, the barrier 154 and the wall 155 are foldable relative to each other along an edge or hinge 170. Therefore, the barrier 154 and/or wall 155 can move between a closed position where the barrier 154 and the wall 155 are in surface to surface contact or are closely adjacent, as shown in FIG. 18, and a deployed position where the barrier 154 extends in front of the wall 155 as shown in FIGS. 16 and 17 for use with a patient.

The user will have a line of sight through the lens, through the aperture 156 of the wall 155 to the patient's eye.

In the same or similar manner as described for fog shields 10, 50, 80, 130, when the fog shield 150 is mounted to a lens, such as lens unit 26, the barrier 154 blocks the exhaled air (e.g. traveling up in the direction I of FIG. 16) from reaching the front lens 34 of the lens unit 26 or at least disperses the exhaled air a sufficient distance from the lens to prevent fogging of, and condensation, on the front 34 of the lens 35. Therefore, the barrier creates a blocked zone 159 above the barrier and in front of the lens. The exhaled air is either trapped below the barrier and/or forced to escape upwards beyond the horizontal boundary provided by the barrier and thus sufficiently distanced from the lens to prevent fogging of, condensation on, and the deposit of debris on the front 34 of the lens unit 26.

The adhesive disclosed for use with one embodiment of the fog shield, can be used with any of the other embodiments of the fog shield herein. In some embodiments, the air barriers of the fog shields may comprise air-impermeable materials, such as plastic.

FIGS. 19 to 22 show a sixth embodiment fog shield 180 for a lens. The fog shield 180 comprises a lens mount 182 and an air barrier 184.

The lens mount 182 comprises a wall 185 with a lens aperture 186. An aperture perimeter wall 188 provides a boundary between the wall 185 and the aperture 186. In some embodiments, the wall 185 comprises a curved perimeter 192, 194.

The barrier 184 extends transverse from the wall 185. The air barrier 184 extends forward from the wall 185. In some embodiments, the barrier 184 is perpendicular to the wall 185. In some embodiments, the barrier 184 is joined or integrally formed with the wall 185. The barrier 184 has a curve from a first side end 196 to an opposite second side end 198. The middle of the barrier 184 is lower than the ends 196, 198.

In some embodiment the transition between the back 184 of the barrier and the front of the wall 185 that meets the back of the barrier is a curved transition 204 rather than a right-angle transition.

The user will have a line of sight through the lens unit 24 (in the direction J), through the aperture 186 of the wall 185 to the patient's eye.

Figure 21:
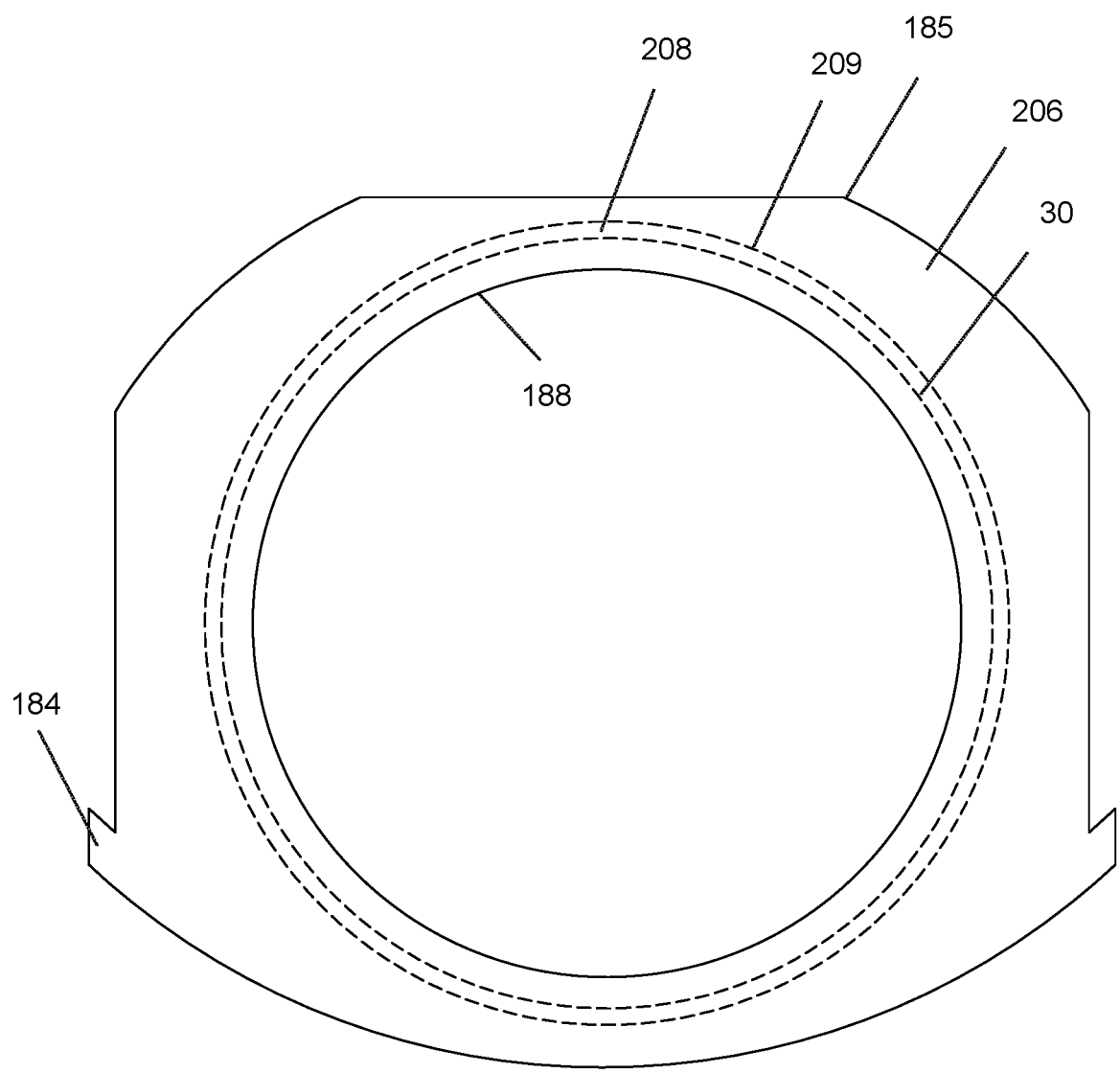
FIG. 21 is a rear view of the fog shield of FIG. 19.

The back side 206 of the wall 185 comprises an adhesive at and/or adjacent the perimeter wall 188. In some embodiments, the back side 206 comprises an adhesive zone 208. The adhesive zone extends between the perimeter wall 188 and an outer edge 209 of the adhesive zone 208. As shown in FIG. 21, the front facing lip or face 30 of the lens unit 26 is within the adhesive zone 208. Therefore, the adhesive at the location(s) of contact between the back wall 206 and the front-facing lip or face 30 of the housing 32 join the fog shield 180 to the lens unit 26. In some embodiments, the adhesive is located in the entire adhesive zone. In some embodiments, the adhesive is located intermittently or at one location within the adhesive zone.

In the same or similar manner as described for fog shields 10, 50, 80, 130, 150, when the fog shield 180 is mounted to a lens, such as lens unit 26, the barrier 184 blocks the exhaled air (e.g. traveling up in the direction K of FIG. 20) from reaching the front lens 34 of the lens unit 26 or at least disperses the exhaled air a sufficient distance from the lens to prevent fogging of, and condensation, on the front 34 of the lens 35. Therefore, the barrier creates a blocked zone 189 above the barrier and in front of the lens. The exhaled air is either trapped below the barrier and/or forced to escape upwards beyond the boundary provided by the barrier and thus sufficiently distanced from the lens to prevent fogging of, condensation on, and the deposit of debris on the front 34 of the lens unit 26.

Figure 23:
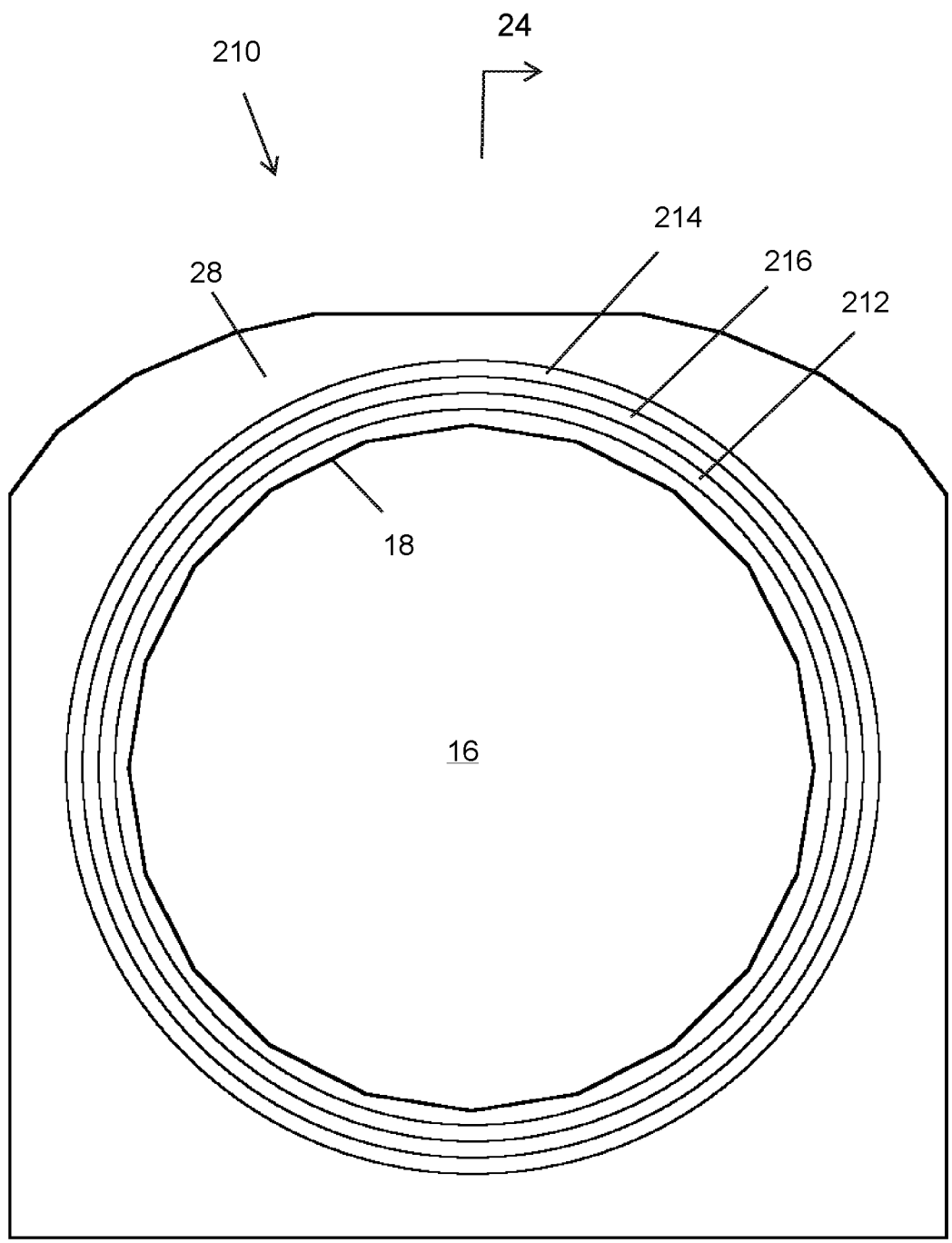
FIG. 23 is a rear view of a seventh embodiment fog shield for a diagnostic ophthalmic lens of the invention.
Figure 24:
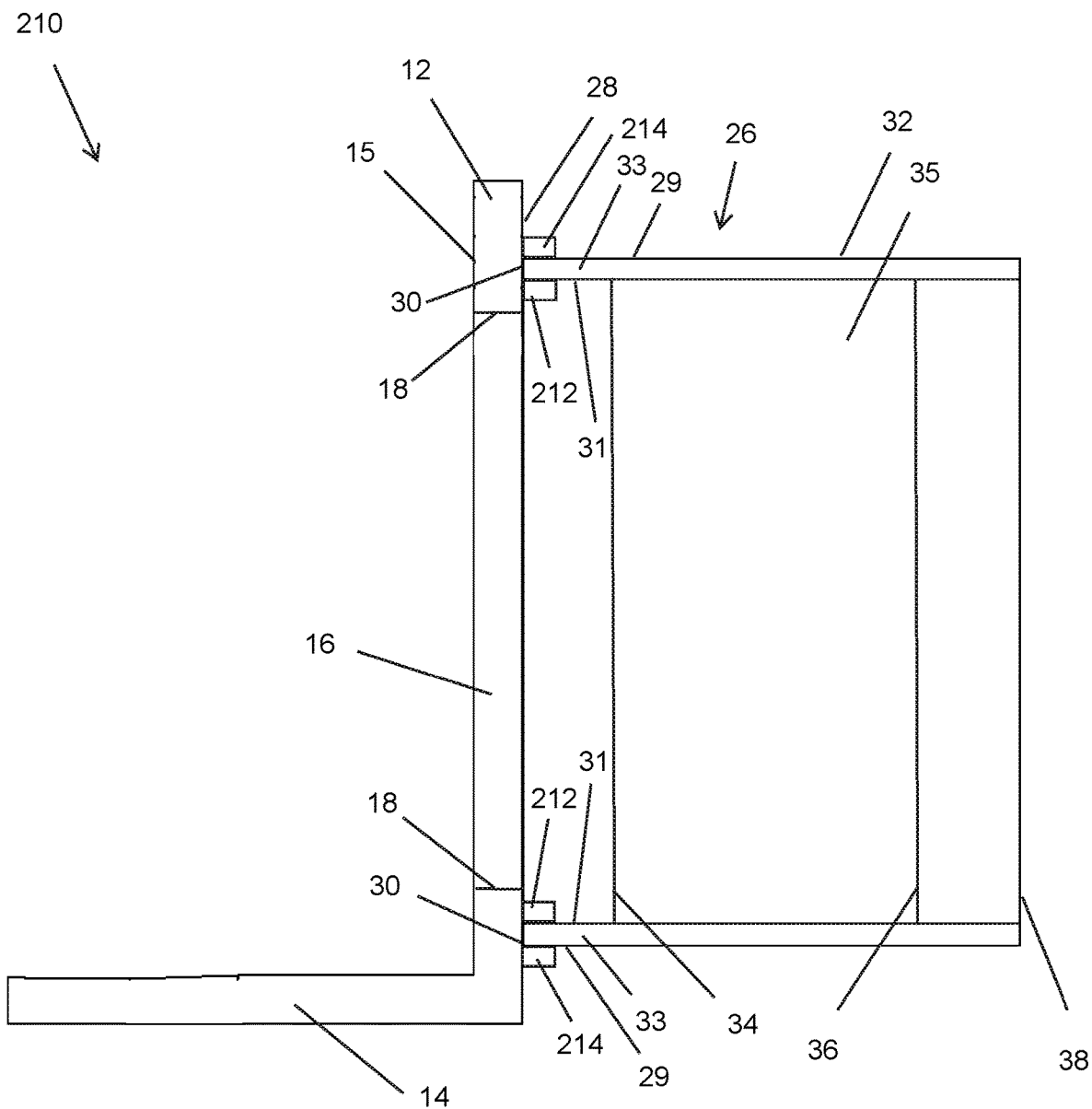
FIG. 24 is a side section view of the fog shield of FIG. 23 and the diagnostic ophthalmic lens of FIG. 2, taken along the plane 24-24 of FIG. 23.

FIGS. 23 and 24 show a seventh embodiment fog shield 210 for a lens. The fog shield 210 is the same and operates the same as fog shield 10, except that the lens mount 12 comprises an interior friction ring 212 on the back wall 28 of the wall 15, instead of or in addition to an adhesive or an adhesive zone, for connecting to the lens unit 26. The friction ring 212 is sized to engage the inside surface 31 of the wall 33 of the housing 32 of the lens unit 26. The ring is sized to friction fit to the wall 33 at the inside surface 31. The friction fit will hold the shield 210 to the lens unit 26.

In some embodiments, instead of the ring 212 completely surrounding the perimeter wall 18, friction blocks are intermittently located at a plurality of locations, such as two, three, four, or more locations, about the aperture 16 for engaging the interior wall of the housing 32. For example, friction blocks, at the location of the ring, could be located at the 12 o'clock and 6 o'clock positions about the aperture 16. As another example, friction blocks can be located at the 2 o'clock, the 6 o'clock, and the 10 o'clock positions about the aperture 16. As a further example, friction blocks can be located at the 12, 3, 6, and 9 o'clock positions about the aperture 16. Therefore, the friction blocks may be formed from a discontinuous ring at the location of ring 212.

In some embodiments, as an alternative or in addition to the interior friction 212, is an exterior friction ring 214 extends from the back wall 28, which is sized to engage the outside surface 29 of the wall 33 of the housing 32 of the lens unit 26. The ring is sized to friction fit to the wall 33 at the outside surface 29. The friction fit will hold the shield 210 to the lens unit 26.

In the embodiment where the interior and exterior friction rings are both used, the wall 33 of the housing 35 will be gripped between the friction rings. FIG. 23 shows the holding location 216 on the back wall 28 where the front face or lip 30 of the wall 33 is received, and in some application and circumstances, is in surface-to-surface contact with the back wall 28.

In some embodiments, instead of the ring 214 completely surrounding the perimeter wall 18, friction blocks are intermittently located at a plurality of locations, such as two, three, four, or more locations, about the aperture 16 for engaging the exterior wall of the housing 32. For example, friction blocks, at the location of the ring, could be located at the 12 o'clock and 6 o'clock positions about the aperture 16. As another example, friction blocks are located at the 2 o'clock, the 6 o'clock, and the 10 o'clock positions about the aperture. As a further example, friction blocks are located at the 12, 3, 6, and 9 o'clock positions about the aperture 16. Therefore, the friction blocks may be formed from a discontinuous ring at the location of ring 214.

In some embodiment, one or more clips are used instead of friction blocks and are placed intermittently in the path of the exterior ring 214 and or the interior ring 212. The clips mechanically hold the fog shield to the housing of the lens unit.

The friction ring 212, 214, the friction blocks, and the clips, as the case may be, can be located about the aperture at the locations so as to receive and hold the desired diagnostic ophthalmic lens.

In some embodiments, one or more friction rings, and/or friction blocks, and/or clips can be used on the fog shields 50, 150, 180, in addition to or in the alternative to using an adhesive to join the lens unit to the fog shield.

Figure 19:
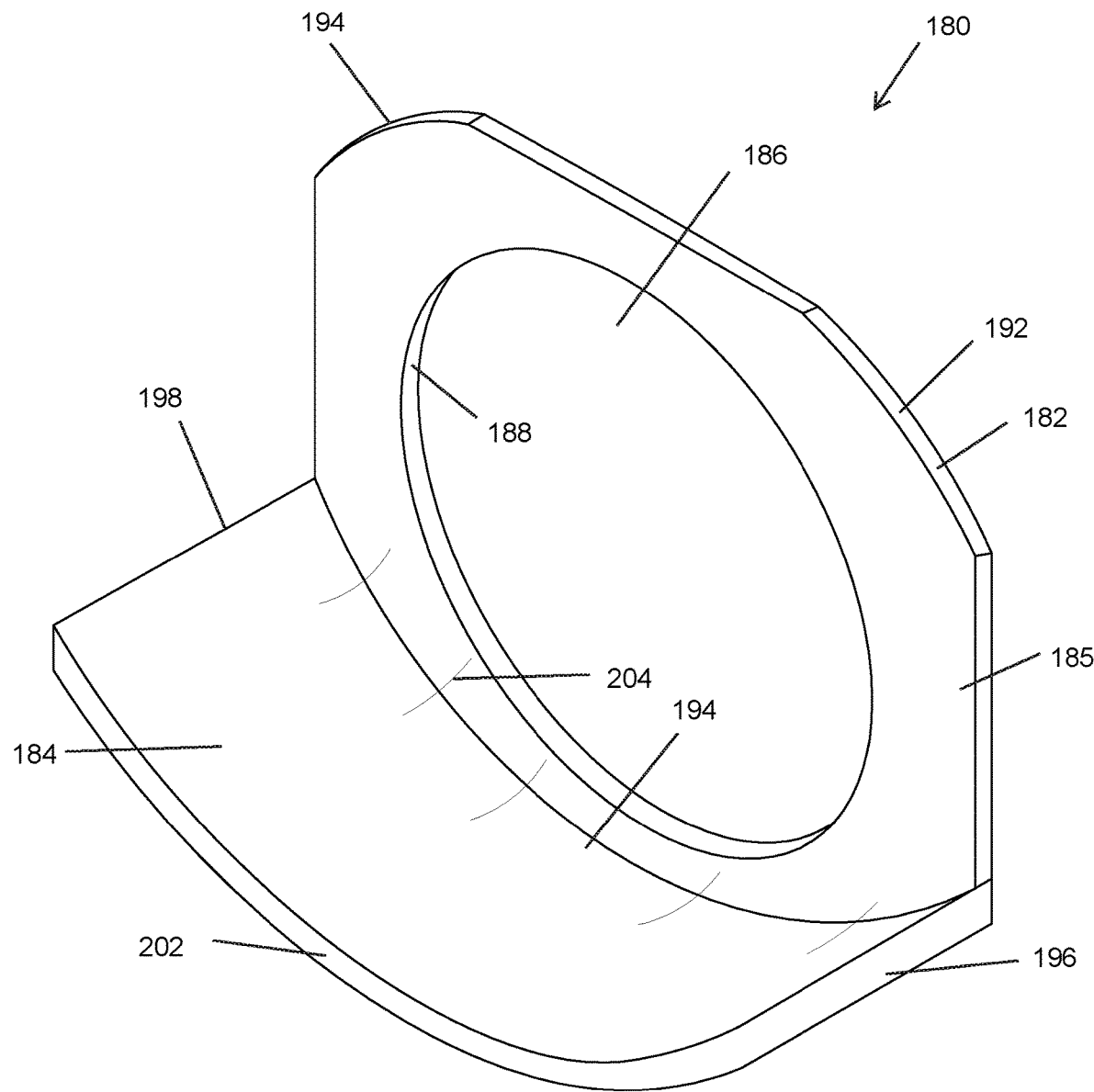
FIG. 19 is a perspective view of a sixth embodiment fog shield for a diagnostic ophthalmic lens of the invention.
Figure 20:
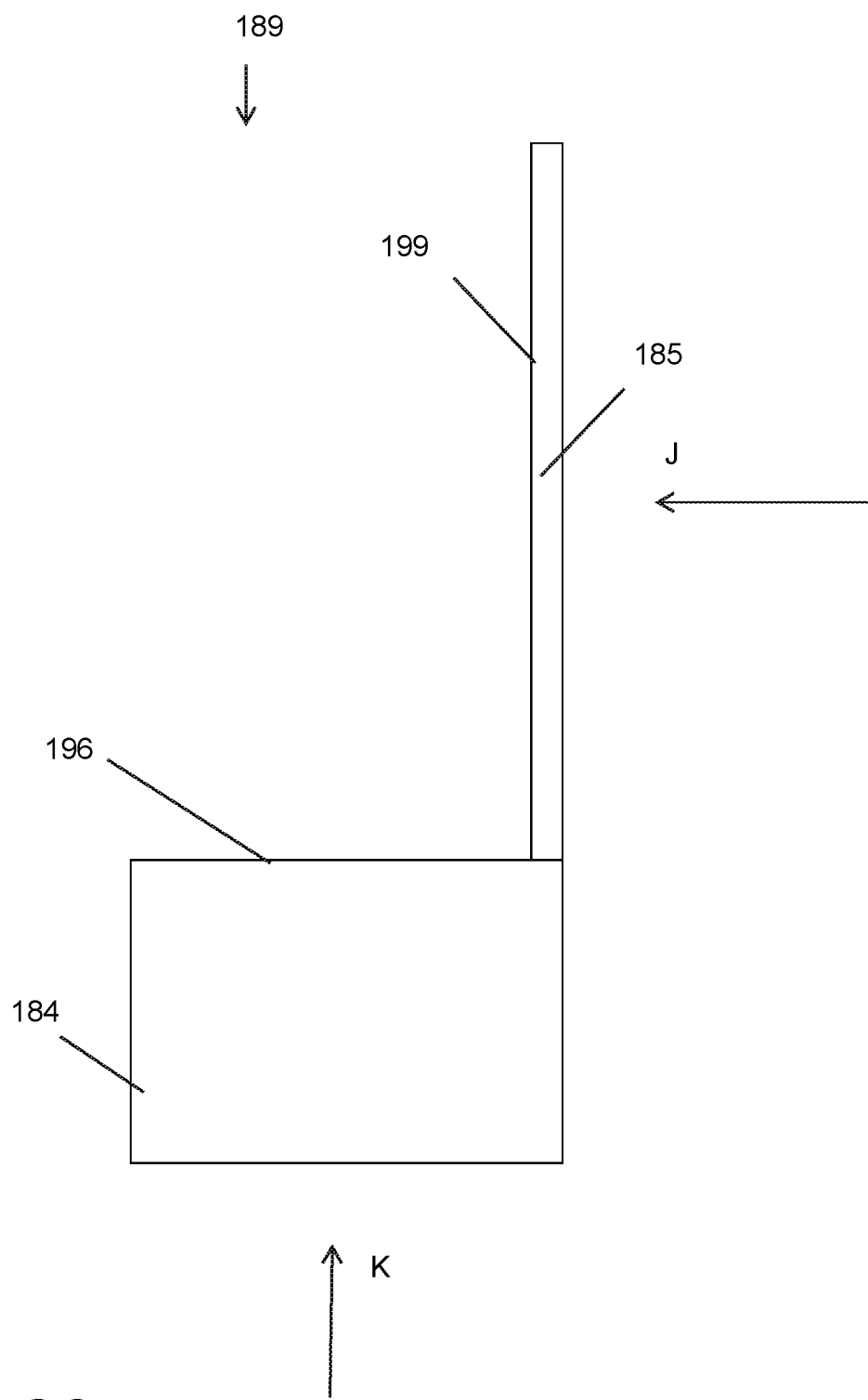
FIG. 20 is a side view of the fog shield of FIG. 19.

In some embodiments, the barrier completely surrounds the lens aperture, rather than only partially surrounding the lens aperture 56, 186 as shown in FIGS. 5 and 19.

In some applications and circumstances, the gap between the patient's mask and the patient's face is at or extends closer to the patient's nose. Therefore, the source of escaping exhaled breath may be closer to one side of the patient's eye and the patient's nose. Therefore, the user may rotate the shield so that the barrier is moved from a horizontal position (or a position where the barrier is centered at 6 o'clock position below the lens aperture) to an angled position (or rotated position) thereby better blocking the exhaled from its source of escape from the mask at or adjacent the patient's nose. The angled or rotated position will position more of the barrier toward or on the side of the patient's eye under examination that is adjacent the patient's nose.

In some embodiments and applications, the lens unit 26 that can be used with the fog shields disclosed herein, comprise the following diagnostic ophthalmic lens models sold by Volk Optical, Inc. of Mentor, Ohio: 90 diopter, 78D, Super 66, 60D, Super field, Super Pupil XL, and Super Vitreo Fundus, and the following diagnostic ophthalmic lens models sold by Ocular Instruments, Inc. of Bellevue, Wash.: 54 diopter, 60D, 66D, 78D, 84D, 90D, 100D, 132D, Maxfield 120D, Maxfield 72D, Maxfield Ultra Mag. These are non-limiting example lenses and other lenses may also be used with the fog shields disclosed herein.

From the foregoing, it will be observed that numerous variations and modifications may be affected without departing from the spirit and scope of the invention. It is to be understood that no limitation with respect to the specific apparatus illustrated herein is intended or should be inferred. For example, one or more component embodiments may be combined, modified, removed, or supplemented to form further embodiments within the scope of the invention. Further, steps could be added or removed from the processes described. Therefore, other embodiments and implementations are within the scope of the invention.

The invention claimed is:

1. A fog preventing shield for a diagnostic ophthalmic lens, comprising:
    a curved air barrier configured to partially but not completely surround a front of a diagnostic ophthalmic lens; and,
    a lens mount connected to the air barrier and configured to connect to the diagnostic ophthalmic lens so that the air barrier is located at least partially below and projects beyond the front of the diagnostic ophthalmic lens when the lens mount is connected to the diagnostic ophthalmic lens.

2. The shield of claim 1, wherein the lens mount comprises a wall comprising a line-of-sight aperture.

3. The shield of claim 2, wherein the wall comprises an adhesive adjacent the aperture for joining the wall to the diagnostic ophthalmic lens.

4. The shield of claim 3 wherein the adhesive extends within an adhesive zone about the aperture.

5. The shield of claim 2, wherein the wall is a mounting wall, the air barrier is a curved wall that is curved along at least a bottom portion of the aperture and transverse to the mounting wall.

6. The shield of claim 2, wherein the wall is transverse to the air barrier.

7. The shield of claim 2, wherein the wall is integrally formed with the air barrier.

8. The shield of claim 1, wherein the air barrier is a curved barrier wall.

9. The shield of claim 8, wherein the barrier wall is wider than the lens mount.

10. The shield of claim 1, wherein the lens mount is an elastic ring.

11. The shield of claim 10, wherein the elastic ring comprises a mounting protrusion and wherein the air barrier comprises a mounting aperture configured to receive the mounting protrusion.

12. The shield of claim 11, wherein the air barrier is pivotal about the mounting protrusion.

13. The shield of claim 11, wherein the mounting protrusion is removably receivable within the mounting aperture.

14. The shield of claim 11, wherein the mounting protrusion comprises a head connected to a shaft, the head has a width that is larger than a width of the shaft and larger than a width of the mounting aperture.

15. The shield of claim 1, wherein the air barrier is removably connected to the lens mount.

16. The shield of claim 1, wherein the lens mount comprises a plurality of lens grippers for gripping a housing of the diagnostic ophthalmic lens.

17. A fog preventing shield for a diagnostic ophthalmic lens, comprising:
a barrier wall; and,
a lens mount connected to the barrier wall, the lens mount transverse to the barrier wall and configured to connect to a diagnostic ophthalmic lens so that the barrier wall is located below and projects beyond a front the diagnostic ophthalmic lens when the lens mount is connected to the diagnostic ophthalmic lens.

18. The shield of claim 17, wherein the lens mount comprises a line-of-sight aperture, the barrier wall is pivotally connected to the lens mount, the barrier wall is movable between a deployed position where the barrier wall projects beyond the front of the diagnostic ophthalmic lens and a closed position where the barrier wall covers the aperture.

19. The shield of claim 17, wherein the barrier wall is wider than the lens mount.

20. Method of preventing fogging of a diagnostic ophthalmic lens, comprising:
mounting an air barrier to a diagnostic ophthalmic lens so that the air barrier is located at least partially below the lens and extends forward from a front of the lens creating a blocked zone above the barrier and in front of the lens,
moving the lens and the barrier toward a patient's eye wherein the barrier blocks a patient's exhaled breath from the blocked zone.

* * * * *